(12) United States Patent
Bhirud et al.

(10) Patent No.: US 8,552,219 B2
(45) Date of Patent: Oct. 8, 2013

(54) PROCESS FOR PREPARING 1-PHENYL-3-DIMETHYLAMINOPROPANE DERIVATIVE

(75) Inventors: Shekhar Bhaskar Bhirud, Punjab (IN); Perminder Singh Johar, Punjab (IN); Sushanta Mishra, Punjab (IN); Danish Jamshad, Punjab (IN)

(73) Assignee: Ind-Swift Laboratories Limited, Chandigarh (IN)

( * ) Notice: Subject to any disclaimer, the term of this patent is extended or adjusted under 35 U.S.C. 154(b) by 0 days.

(21) Appl. No.: 13/824,210

(22) PCT Filed: Sep. 20, 2011

(86) PCT No.: PCT/IN2011/000646
§ 371 (c)(1),
(2), (4) Date: Mar. 15, 2013

(87) PCT Pub. No.: WO2012/038974
PCT Pub. Date: Mar. 29, 2012

(65) Prior Publication Data
US 2013/0190522 A1  Jul. 25, 2013

(30) Foreign Application Priority Data
Sep. 20, 2010  (IN) .......................... 2232/DEL/2010

(51) Int. Cl.
*C07C 209/70* (2006.01)
*C07C 309/73* (2006.01)

(52) U.S. Cl.
USPC .............................. 564/375; 564/358; 558/52

(58) Field of Classification Search
USPC .................................. 564/358, 375; 558/52
See application file for complete search history.

(56) References Cited

U.S. PATENT DOCUMENTS

| 6,248,737 B1 | 6/2001 | Buschmann et al. |
| RE39,593 E | 4/2007 | Buschmann et al. |
| 7,417,170 B2 | 8/2008 | Hell et al. |
| 2006/0167318 A1 | 7/2006 | Jagusch et al. |

FOREIGN PATENT DOCUMENTS

| EP | 0693475 A | 1/1996 |
| EP | 0799819 A | 10/1997 |
| WO | 2004108658 A | 12/2004 |
| WO | 2008012046 A | 1/2008 |
| WO | 2008012283 A | 1/2008 |

OTHER PUBLICATIONS

International Search Report for PCT/IN2011/000646 dated Feb. 9, 2012.

*Primary Examiner* — Kristin Vajda
(74) *Attorney, Agent, or Firm* — Kramer Amado, P.C.

(57) ABSTRACT

Provided is a process for the preparing 1-phenyl-3-dimethylaminopropane derivatives of formula I, (The formula should be inserted here) and its pharmaceutically acceptable salts thereof via novel intermediates.

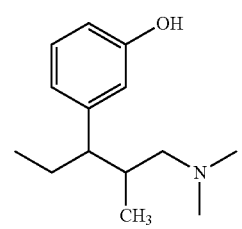

(I)

20 Claims, No Drawings

1

PROCESS FOR PREPARING L-PHENYL-3-DIMETHYLAMINOPROPANE DERIVATIVE

FIELD OF THE INVENTION

The present invention relates to a process for preparing 1-phenyl-3-dimethylaminopropane derivatives of formula I,

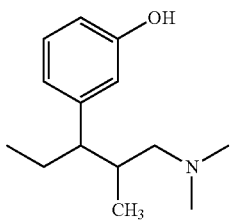

Formula I and its pharmaceutically acceptable salts thereof.

Specifically, present invention provides a process for preparing tapentadol of formula Ia,

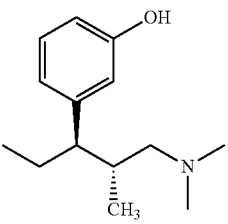

Formula Ia and its pharmaceutically acceptable salts thereof via novel intermediates.

BACKGROUND OF THE INVENTION

Tapentadol of formula Ia, marketed as its hydrochloride salt under the trade name

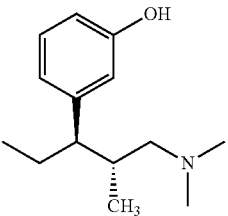

Formula Ia

Nucynta, is a centrally-acting analgesic and is chemically known as 3-[(1R,2R)-3-(dimethylamino)-1-ethyl-2-methyl-propyl]phenol.

It has a unique dual mode of action as an agonist at the g-opioid receptor and as a norepinephrine reuptake inhibitor. μ-Opioid agonists are drugs that bind to and activate μ-opioid receptors in the central nervous system. These drugs modify sensory and affective aspects of pain, inhibit the transmission of pain at the spinal cord and affect activity parts of the brain that control how pain is perceived. Norepinephrine reuptake inhibitors are a type of central nervous system medication that increases the level of norepinephrine in the brain by inhibiting its re-absorption into nerve cells; these compounds have analgesic properties.

Tapentadol and its analogues are first disclosed in U.S. Pat. No. RE 39,593 (reissue of U.S. Pat. No. 6,248,737). According to the process disclosed in above patent, tapentadol, is prepared by process as shown in the following scheme:

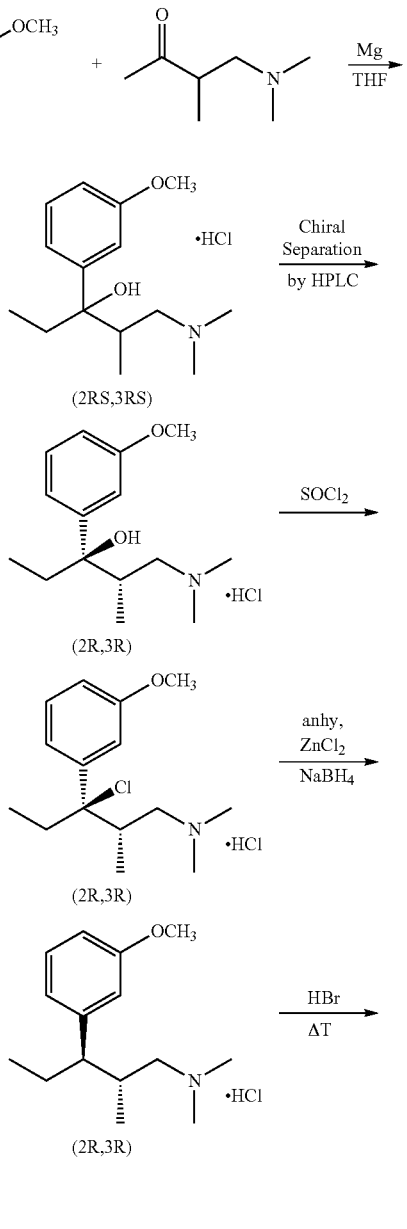

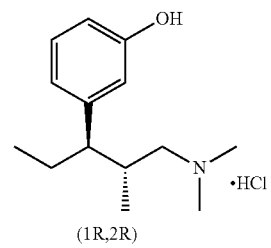

Tapentadol is prepared by starting from 3-bromoanisole and 1-dimethylamino-2-methylpentan-3-one. 3-Bromoanisole is reacted with 1-dimethylamino-2-methylpentan-3-one to form racemic tertiary alcohol intermediate, which is then resolved by chiral HPLC. The resolved intermediate is then converted into corresponding chloride compound, followed by reduction with zinc borohydride, zinc cyanoborohydride or tin cyanoborohydride and then finally converted into tapentadol by demethylation using hydrobromic acid. The process involves formation of hydrochloride salts of intermediates which are then used in the next stage. Hydrochloride formation of intermediates is carried out in the presence of trimethylchlorosilane, which is a highly flammable liquid and being hazardous, hence not advisable to use in the industrial scale. The other disadvantage of the above process is resolution by the chiral HPLC, which is not amenable for industrial level synthesis.

U.S. Pat. No. 7,417,170 discloses a process for the preparation of racemic 3-(3-methoxyphenyl)-N,N,2-trimethylpentanamine, an intermediate of tapentado,1 by the reaction of (2S,3S)-1-(dimethylamino)-3-(3-methoxyphenyl)-2-methyl-3-pentanol with an acid to form a mixture of cis and trans isomer of alkene intermediate, the resulting mixture is then hydrogenated to form a mixture of (2R,3R) and (2R,3S)-3-(3-methoxyphenyl)-N,N,2-trimethylpentanamine as outlined below.

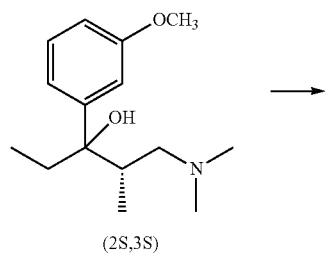

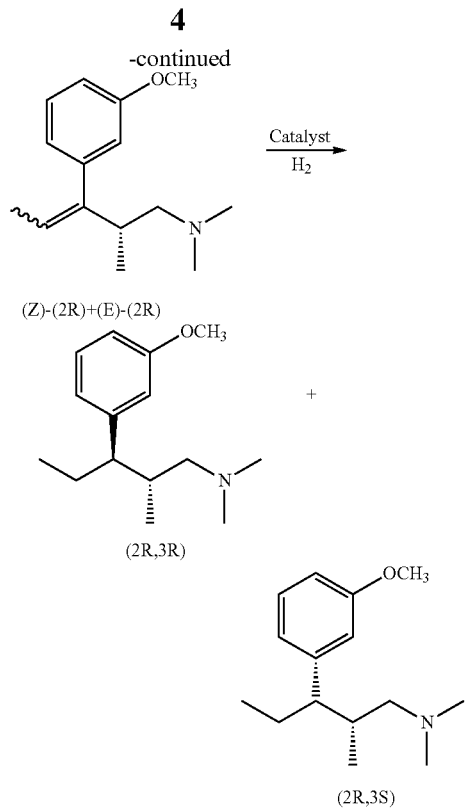

US patent publication 2006/0167318 discloses a process for the preparation of racemic 3-(3-methoxyphenyl)-N,N,2-trimethylpentanamine, an intermediate of tapentadol, by dehydrating corresponding (2S,3S) tertiary alcohol intermediate, followed by reduction of resulting alkene intermediate using heterogeneous catalyst to form a mixture of (2R,3R) and (2R,3S)-3-(3-methoxyphenyl)-N,N,2-trimethylpentanamine as outlined below.

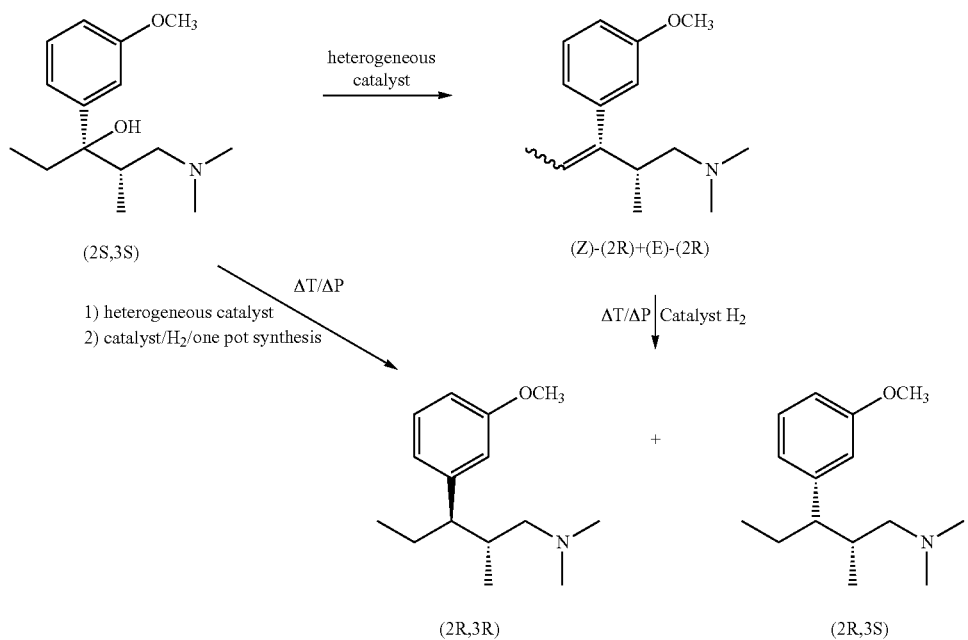

PCT publication WO 2008/012283 discloses a process for the preparation of (2R,3R)-3-(3-methoxyphenyl)-N,N,2-trimethylpentanamine, an intermediate of tapentadol, by treating corresponding hydroxy compound with acid chloride, ethyl oxalyl chloride or trifluoro acetic acid anhydride, then converted to (2R,3R)-3-(3-methoxyphenyl)-N,N,2-trimethylpentanamine or its acid addition salts as outlined below.

Another object of the present invention is to provide a process for preparing tapentadol of formula Ia or its pharmaceutically acceptable salts thereof using novel intermediates.

Yet another object of the present invention is to provide novel intermediates and processes for preparing the same. These intermediates are useful in the preparation of 1-phenyl-

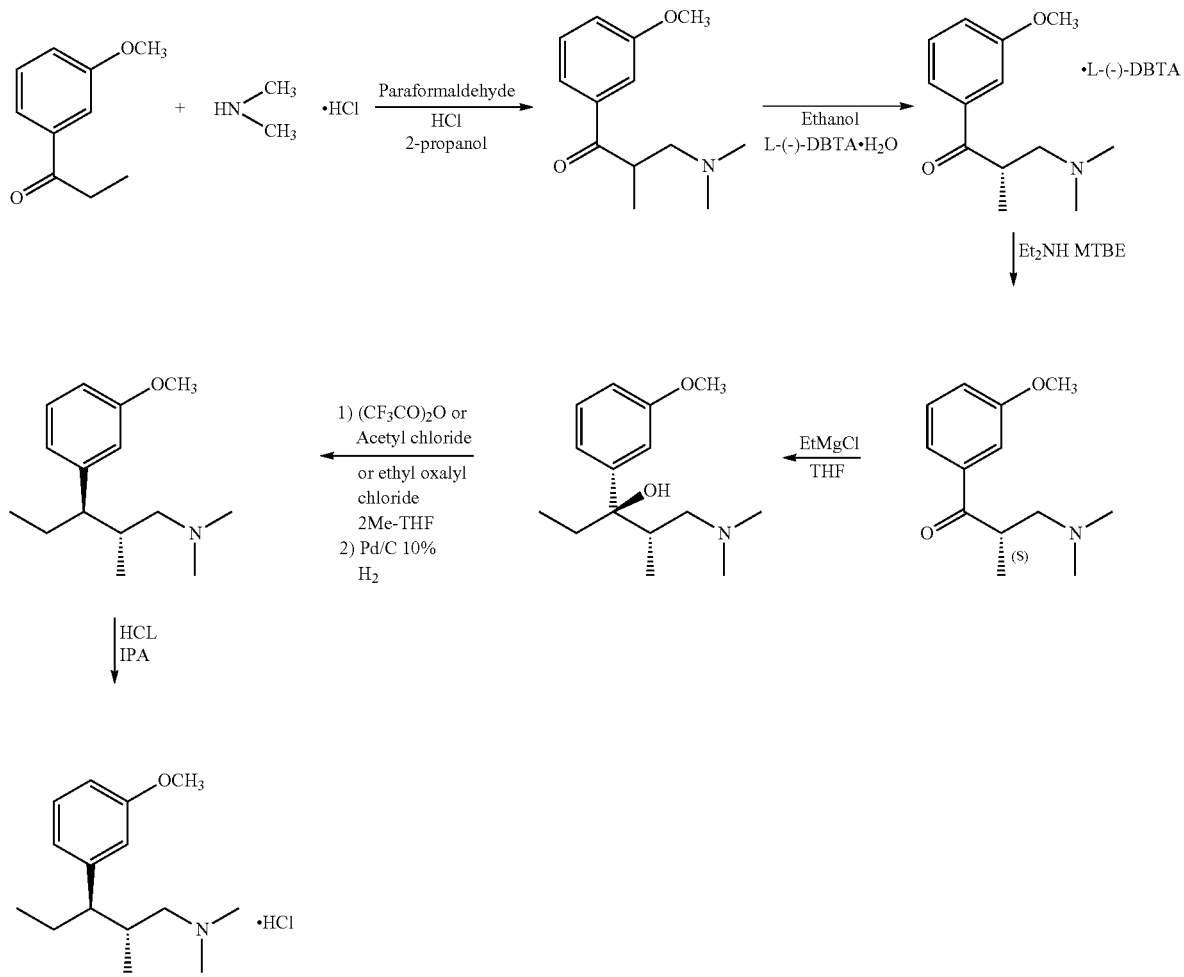

In view of the above, there is an urgent need to develop a cost effective and industrially advantageous process for the synthesis of 1-phenyl-3-dimethylaminopropane derivatives. Thus, present invention fulfills the need in the art and provides an industrially advantageous process for preparing 1-phenyl-3-dimethylaminopropane derivatives, in particular tapentadol and its pharmaceutically acceptable salts thereof that does not involve chiral chromatographic technique for separation of isomers.

OBJECT OF THE INVENTION

It is the principal object of the present invention to provide an industrially advantageous process for preparing 1-phenyl-3-dimethylaminopropane derivatives of formula I, including its isomers, stereoisomer, enantiomers, diastereomers, racemates, solvates, hydrates or pharmaceutically acceptable salts thereof using novel intermediates.

3-dimethylaminopropane derivatives of formula I and its pharmaceutically acceptable salts thereof.

SUMMARY OF THE INVENTION

Accordingly, the present invention provides a novel and industrially advantageous process for preparing 1-phenyl-3-dimethylaminopropane derivatives of formula I,

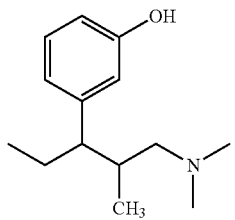

Formula I including its isomers, stereoisomer, enantiomers, diastereomers, racemates, solvates, hydrates or pharmaceutically acceptable salts thereof, preferably tapentadol of formula Ia,

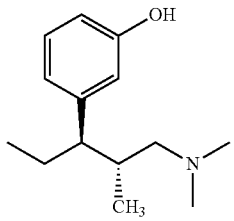

Formula Ia or pharmaceutically acceptable salts thereof.

According to one embodiment, present invention provides a process for the preparation of 1-phenyl-3-dimethylaminopropane derivatives of formula I, or its isomers, enantiomers, diastereomers, racemates, solvates, hydrates or pharmaceutically acceptable salts thereof, comprising the steps of:

a). converting 1-(3-hydroxy-phenyl)-propan-1-one of formula II,

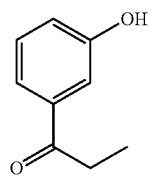

Formula II in to a compound of general formula III,

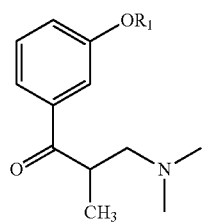

Formula III wherein $R_1$ can be selected —$SO_2R_2$; wherein $R_2$ can be selected from hydrogen, straight chain or branched alkyl, aryl, aralkyl, alkaryl, heteroalkyl, heteroaryl and the like which can be substituted or unsubstituted b). reacting the compound of formula III with a suitable reagent under Grignard reaction conditions to give a hydroxyl compound of formula IV,

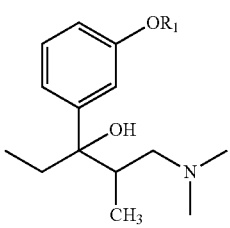

Formula IV wherein $R_1$ is as defined above c). optionally, reacting hydroxyl compound of formula IV with a suitable acid to form corresponding salt of compound of formula IV;

d). dehydrating hydroxyl compound of formula IV or salt thereof using a suitable dehydrating agent to give an alkene compound of formula V,

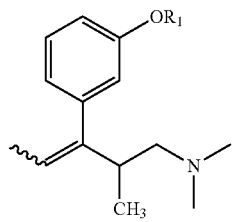

Formula V wherein $R_1$ is as defined above e). hydrogenating alkene compound of formula V using a suitable reagent to give a compound of formula VI,

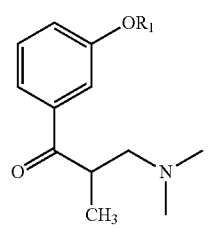

Formula VI wherein $R_1$ is as defined above f). deprotecting compound of formula VI with a suitable deprotecting reagent to give a compound of formula I or pharmaceutically acceptable salts thereof.

According to another embodiment, present invention provides a process for the preparation of tapentadol of formula Ia or pharmaceutically acceptable salts thereof, comprising the steps of a). converting 1-(3-hydroxy-phenyl)-propan-1-one of formula II,

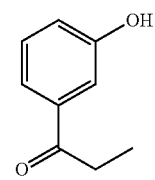

Formula II in to a compound of general formula III,

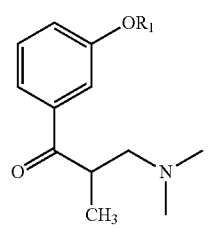

Formula III wherein $R_1$ is as defined above b). resolving compound of formula III using a suitable resolving agent to form a chiral compound of formula IIIa,

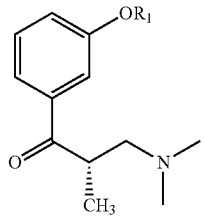

Formula IIIa wherein $R_1$ is as defined above c). reacting compound of formula IIIa with a suitable reagent under Grignard reaction conditions to give a hydroxyl compound of formula IVa,

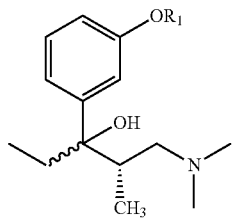

Formula IVa wherein $R_1$ is as defined above d). optionally, reacting hydroxyl compound of formula IVa with a suitable acid to form corresponding salt of compound of formula IVa;

e). dehydrating hydroxyl compound of formula IVa or salts thereof using a suitable dehydrating agent to give an alkene compound of formula Va,

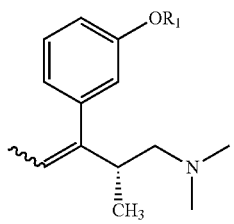

Formula Va wherein $R_1$ is as defined above f). hydrogenating alkene compound of formula Va using a suitable reagent to give a compound of formula VIa,

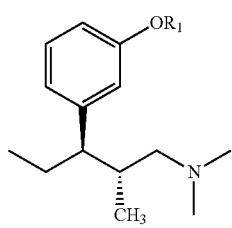

Formula VIa wherein $R_1$ is as defined above g). optionally, purifying compound of formula VIa, h). deprotecting compound of formula VIa with a suitable deprotecting reagent to give tapentadol of formula Ia or pharmaceutically acceptable salts thereof.

According to another embodiment, present invention provides a process for the conversion of 1-(3-hydroxy-phenyl)-propan-1-one of formula II in to a compound of formula III, comprising the steps of:

a). protecting hydroxyl group of 1-(3-hydroxy-phenyl)-propan-1-one of formula II to form compound of formula VII,

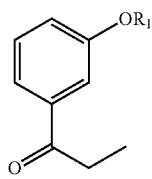

Formula VII wherein $R_1$ is as defined above
using a suitable reagent; and b). aminomethylating compound of formula VII with a suitable aminomethylating agent to form a compound of formula III; and c). optionally, further resolving compound of formula III to form a chiral compound of formula IIIa.

According to another embodiment, present invention provides a process for the conversion of 1-(3-hydroxy-phenyl)-propan-1-one of formula II in to a compound of formula III, comprising the steps of:

a). aminomethylating 1-(3-hydroxy-phenyl)-propan-1-one of formula II with a suitable aminomethylating agent to form compound of formula VIII,

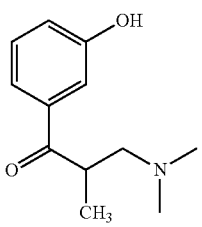

Formula VIII wherein $R_1$ is as defined above b). protecting hydroxyl group of compound of formula VIII using a suitable reagent to form a compound of formula III; and c). optionally, further resolving compound of formula III to form compound of formula IIIa.

According to still another embodiment, present invention provides novel intermediate of formula III, IV, V, VI, VII and VIII including isomers, stereoisomers, enantiomers, diastereomers, racemates, solvates, hydrates or salts thereof.

According to another embodiment, present invention provides novel intermediates of formula IIIa, IVa, Va, VIa including solvates, hydrates or salts thereof.

DETAILED DESCRIPTION OF THE INVENTION

As used herein "the compound of formula I" or "1-phenyl-3-dimethylaminopropane derivative of formula I" as well as "all the intermediates" used herein includes in each case one of its pure stereoisomer, enantiomer, diastereomer, or racemates, or mixture of stereoisomer, mixture of enantiomer, mixture of diastereomer in any ratio, salts, solvates, and hydrates thereof".

The present invention provides a process for the preparation 1-phenyl-3-dimethylaminopropane derivative of formula I, or pharmaceutically acceptable salts thereof using novel intermediates.

Specifically present invention provides a process for the preparation of tapentadol of formula Ia or its pharmaceutically acceptable salts thereof from corresponding desired isomer of the novel intermediates and/or salts thereof or by performing resolution after the synthesis of racemic final compound of formula I.

According to one embodiment, present invention provides a process for the preparation of 1-phenyl-3-dimethylaminopropane derivatives of formula I by initially converting compound of formula II in to a compound of formula III.

Compound of formula II can be converted in to a compound of formula III either by first protecting the hydroxyl group followed by aminomethylation; or vice versa.

According to one method, compound of formula II is first reacted with a suitable reagent to form hydroxyl protected intermediate of formula VII which is then converted to a compound of formula III.

Generally, the process involves reaction of compound of formula II with a suitable reagent in the presence of a base at a temperature of −10 to 80° C. for few minutes to several hours. Suitable reagent used for the reaction can be selected from reagents known in the art that can effectively protect the hydroxyl group with —$SO_2R_2$ (wherein $R_2$ is as defined above). Preferably suitable reagent can be selected amongst (substituted or unsubstituted) straight chain or branched alkyl, aryl, aralkyl, alkaryl, heteroalkyl or heteroaryl sulfonyl halide such as p-toluenesulfonyl halide, benzenesulfonyl halide, ortho, meta or para-chlorobenzenesulfonyl halide, methanesulfonyl halide; (substituted or unsubstituted) straight chain or branched, alkyl, aryl, aralkyl, alkaryl, heteroalkyl or heteroaryl sulfonyl anhydride; and the like. Suitable base employed for the reaction can be organic or inorganic base. Organic base used for the reaction can be organic amine of general formula NR'R"R''' (wherein R', R" and R''' can be same or different and can be independently selected from alkyl, aryl, aralkyl, alkaryl, heteroalkyl or heteroaryl and the like). Preferably organic base can be selected from trialkylamine such as triethylamine, diisopropylethylamine and the like or combination thereof. Inorganic base can be selected from alkali or alkaline metal hydroxide, carbonates, bicarbonate, hydrides, alkoxides such as lithium hydroxide, sodium hydroxide, potassium hydroxide, sodium carbonate, potassium carbonate, lithium carbonate, sodium bicarbonate, potassium bicarbonate, lithium bicarbonate and the like or combination thereof. The reaction can be carried out using a suitable solvent for employing the reaction medium. Suitable solvent includes halogenated solvent such as dichloromethane, chloroform; $C_{4-14}$ ethers such as isopropyl ether, methyl tertiary butyl ether, 1,2-dimethoxy ethane, dioxane, 2-methyl tetrahydrofuran, cyclopentylmethyl ether; $C_{6-14}$ aromatic hydrocarbon such as toluene, xylene, ethylbenzene; $C_{3-10}$ ketone such as acetone, methyl ethyl ketone, methyl isobutyl ketone; $C_{3-12}$ ester such as ethyl acetate, methyl acetate, isopropyl acetate and the like or mixture thereof. Reaction can be further optionally carried out using a catalyst such as dimethylaminopyridine or a phase transfer catalyst which includes tetrabutylammonium bromide, benzyl triethyl ammonium chloride, cetyl trimethyl ammonium bromide and the like to enhance the kinetics of the reaction. Usually reaction can be carried out at a temperature of −10 to 80° C. for 1 to 24 hours, preferably till completion of reaction. The progress of reaction can be monitored by suitable techniques such as high pressure liquid chromatography (HPLC), thin layer chromatography (TLC), gas chromatography (GC), ultra pressure liquid chromatography (UPLC) and the like. After completion of reaction, the desired product of formula VII can be isolated from reaction mixture using suitable techniques or can be in situ used for next reaction. Preferably, compound of formula VII can be isolated from the reaction mixture by removal of solvent from the reaction mixture using distillation, evaporation and the like. Compound of formula VII can be optionally purified with a suitable solvent which includes aliphatic or aromatic hydrocarbon such as cyclohexane; $C_{4-14}$ ether; ketones, nitriles, halogenated solvent, alcohol and the like or mixture thereof. Product can be isolated from the mixture using suitable techniques such as filtration, centrifugation and the like.

Compound of formula VII can be converted to compound of formula III by aminomethylation of compound of formula VII.

Generally, process involves the reaction of compound of formula VII with a suitable aminomethylating agent at a temperature of 0° C. to reflux temperature till the completion of the reaction. Aminomethylating agent includes but not limited to formaldehyde and dimethyl amine or N-methyl-N-methylenemethane ammonium halide and acetyl halide. Usually, reaction can be carried out at a temperature of 0° C. to reflux temperature for few minutes to several hours, preferably at a temperature of 30 to 140° C. for 1 hour to 30 hours. The reaction can be accomplished in the presence of a suitable catalyst. Formaldehyde can be used as paraformaldehyde or formalin. Suitable catalyst includes inorganic acid such as hydrochloric acid, hydrobromic acid, sulfuric acid, phosphoric acid, nitric acid, hypochloric acid; organic acid such as $C_{1-20}$ carboxylic acid like formic acid, acetic acid etc. Dimethyl amine employed for the reaction can be used as such or in the form of salt. The salt of dimethyl amine employed for the reaction can be with organic acid which includes carboxylic acid such as formic acid, acetic acid, oxalic acid and the like; or inorganic acid such as hydrochloric acid, hydrobromic acid and the like or combination thereof. Solvent used for carrying out the reaction includes alcohol such as methanol, ethanol, isopropanol; $C_{4-14}$ ethers such as isopropyl ether, methyl tertiary butyl ether, 1,2-dimethoxy ethane, dioxane, 2-methyl tetrahydrofuran, cyclopentylmethyl ether; $C_{6-14}$ aromatic hydrocarbon such as toluene, xylene, ethylbenzene; halogenated solvent such as dichloromethane, chloroform; $C_{3-12}$ ester such as ethyl acetate, methyl acetate, isopropyl acetate and the like or mixture thereof. After completion of the reaction, compound of formula III can be isolated from the reaction mixture by any conventional method or can be used in situ for the further reaction. Thereafter, reaction mixture can be optionally cooled to a temperature of 0 to 35° C. Specifically, compound of formula III can be isolated from the reaction mixture by generating biphasic reaction mixture by the addition of water and water immiscible solvent to the reaction mixture. Water immiscible solvent includes aliphatic hydrocarbon such as cyclohexane, n-hexane, n-heptane; halogenated solvent such as dichloromethane, chloroform; ethers such as isopropyl ether, methyl tertiary butyl ether, 2-methyl tetrahydrofuran, methyl cyclopentylether; aromatic hydrocarbon such as toluene, xylene, ethylbenzene and the like or mixture thereof. Compound of formula III can be recovered from the aqueous layer by adding a suitable base followed by extraction with water immiscible solvent in which product has more solubility. Suitable base used can be a strong base or a weak base selected from an organic base including trialkylamine such as triethylamine and the like; or inorganic base including alkali or alkaline metal hydroxide, carbonates, bicarbonate, or combination thereof such as sodium hydroxide, sodium carbonate, potassium hydroxide, potassium carbonate, lithium carbonate, lithium hydroxide and the like or combination thereof. Water immiscible solvents are same as defined above. The desired product can be recovered from resulting organic layer using suitable techniques such as evaporation, distillation and the like.

According to another method, compound of formula II is first converted to intermediate of formula VIII which is then reacted with a suitable reagent to protect hydroxyl group and form compound of general formula III.

Generally, process involves the reaction of compound of formula II with a suitable aminomethylating agent at a temperature of 0° C. to reflux temperature for few minutes to several hours, preferably at a temperature of 20 to 140° C. for 1 hour to 48 hours to form compound of formula VIII. Suitable aminomethylating agent includes but not limited to formaldehyde and dimethyl amine or N-methyl-N-methylenemethane ammonium halide and acetyl halide. The reaction can be accomplished in the presence of a suitable catalyst. Suitable catalyst, solvent and other reaction condition employed for the reaction are same as described above for the similar condensation reaction. After the completion of the reaction, compound of formula VIII can be isolated from the reaction mixture by using conventional methods or can be proceed as such for the further reaction.

The compound of formula VIII thus prepared is then reacted with a suitable reagent to protect the hydroxyl group present in the compound of formula VIII to form a compound of general formula III.

Generally, the process involves reaction of compound of formula VIII with a suitable reagent in the presence of a base at a temperature of −10 to 80° C. for few minutes to few hours. Suitable reagent, solvent and reaction condition employed for reaction are same as described above for the similar hydroxyl protection reaction. After completion of reaction, compound of formula III can be isolated from the reaction mixture by using conventional methods or can be used as such for further reaction.

Compound of formula III, prepared by the process of present invention can be used as such for further reaction or can be first resolved to form a specific desired enantiomer.

Compound of formula III can be optionally resolved using a suitable resolving agent to separate enantiomers of compound of formula III which can be employed for further reaction and yield the corresponding diastereomer of final compound of formula I or pharmaceutically acceptable salts thereof.

Generally, compound of formula III can be resolved using a suitable resolving agent in a suitable solvent at a temperature of −20 to 120° C. for a time sufficient for the separation of desired isomer, preferably resolution reaction can be carried out for 0.5 to 36 hours. Suitable resolving agent can be selected from the resolving agents known in the art that can effectively produce the desired isomer and can be selected depending upon the enantiomer required. Specifically, resolving agent can be selected amongst but not limited to chiral acid selected from the group consisting of dibenzoyl tartaric acid, camphor sulfonic acid, tartaric acid, di-tolyl tartaric acid, mandelic acid and the like. Choice of isomer of resolving agent depends upon the nature of enantiomer desired and also depends upon the ability of the enantiomeric salt formation of compound of formula III. The solvent employed during resolution is not critical, thus a suitable solvent can be selected on the basis of solubility of enantiomeric salts.

Specifically suitable solvent can be selected from $C_{4-14}$ ether such as 1,2-dimethoxyethane, dioxane, 2-methyl tetrahydrofuran, isopropylether, methyl tertiary butyl ether, tetrahydrofuran; $C_{3-12}$ ketone such as acetone, methylisobutyl ketone, methylethyl ketone; $C_{1-10}$ alcohols such as methanol, ethanol, isopropanol; nitriles such as acetonitrile, propionitrile; esters such as ethyl acetate, isopropyl acetate; aliphatic or aromatic hydrocarbon such as pentane, cyclohexane, n-hexane, n-heptane, toluene, xylene, ethylbenzene and the like or mixture thereof. The separation may result simply by stirring at a suitable temperature in a solvent until one of the salts preferentially precipitate out. After completion of salt formation, desired enantiomeric salt can be separated from the reaction mixture using suitable techniques such as filtration, centrifugation and the like.

Enantiomeric salt thus separated can optionally be purified to enhance the chiral purity of the compound. Purification of enantiomeric salt can be optionally carried out by employing one or more purification method selected from crystallization, slurry wash or stirring in a suitable solvent. Solvent can be selected depending upon the nature of purification employed as well as on the nature of the enantiomerically salt. Preferably, solvent can be selected amongst but not limited to ethers such as tetrahydrofuran, 1,2-dimethoxyethane; ester such as ethyl acetate; aliphatic or aromatic hydrocarbon such as toluene, xylene, ethylbenzene, halogenated solvents such as dichloromethane, chloroform; nitriles such a acetonitrile; alcohols such as methanol, ethanol, isopropanol; ketone such as acetone, methyl isobutyl ketone, water and the like or mixture thereof in any suitable proportion. Specifically, enantiomeric salt of compound of formula III can be stirred in a suitable solvent at a temperature of 20 to 90° C. for 1 to 36 hours. Mixture can be optionally cooled to a temperature of −10° C. to ambient temperature prior to isolation of desired compound. Purified enantiomeric salt of compound of formula III can be isolated from the mixture by suitable techniques such as filtration, centrifugation and the like.

Enantiomeric salt of compound of formula III can be hydrolyzed to form free base of corresponding enantiomer of formula III.

Generally, hydrolysis of enantiomeric salt of compound of formula III can be carried out using a suitable base in a solvent at a temperature of −10 to 50° C. for 1 to 10 hours, preferably till the complete hydrolysis take place. Suitable base can be an organic or an inorganic base. Organic base used for the reaction can be amine of general formula NR'R"R'" (wherein R', R" and R'" are as defined above) such as ammonia, monoalkyl, dialkyl or trialkylamine and the like. Inorganic base can be selected from alkali or alkaline metal hydroxide, carbonates, bicarbonate, hydride, alkoxides thereof such as lithium hydroxide, potassium hydroxide, sodium carbonate, potassium carbonate, lithium carbonate, sodium bicarbonate, potassium bicarbonate, lithium bicarbonate and the like or combination thereof. Solvent used for the reaction depends upon the nature of chiral isomer of the compound of formula III.

Preferably solvent employed selected from the solvents in which desired isomer is having high solubility. Solvent includes halogenated solvent such as dichloromethane, chloroform; ester such as ethyl acetate; ethers such as methyl tertiary butyl ether, isopropyl ether; aliphatic or aromatic hydrocarbon such as toluene; and the like or mixture thereof. Specific isomer of compound of formula III can be isolated from resulting organic layer by methods such as distillation, evaporation and the like.

Compound of formula III can be resolved to form either (S)-isomer or (R)-isomer which may contain small amount of other enantiomer as an impurity. The specific enantiomer i.e. (S)-isomer or (R)-isomer of compound of formula III can be optionally purified to enhance the enantiomeric excess and minimize the presence of undesired isomer. Preferably, compound of formula III can be resolved to provide (S)-isomer of compound of formula III represented here as compound of formula IIIa, which can be used for the further reaction to yield final compound as tapentadol or pharmaceutically acceptable salts thereof.

Alternatively, compound of formula VIII can be resolved to provide a specific enantiomer ((S) or (R) isomer which may or may not contain isomeric impurities) which is then converted to corresponding enantiomer of compound of formula III by protection of hydroxyl group using a suitable reagent and reaction conditions as specified above.

Compound of formula III or isomers thereof is then reacted with a suitable reagent under Grignard reaction condition to form hydroxyl compound of formula IV.

Generally, process involves the reaction of compound of formula III with a suitable reagent at a temperature of −30 to 50° C. for 1 hour to 48 hours. Suitable reagent used for the reaction can be organometallic compound of ethyl halide or other organometallic compound such as ethyl lithium and the like. Metal used in organometallic compound can be selected from magnesium, lithium, sodium, aluminium and the like. Preferably, reagent used for the reaction is selected from ethyl magnesium halide, ethyl lithium and the like. The reaction can be optionally further carried out in the presence or absence of a catalyst selected from Lewis acid catalyst such as metal halide like cuprous halide, zinc halide, nickel halide, cobalt halide; or inorganic salts. Reaction can be carried out in the presence of a suitable solvent for providing the reaction media. Suitable solvent includes ether such as tetrahydrofuran, diethyl ether, isopropyl ether, methyl tertiary butyl ether, dioxane, 1,2-dimethoxyethane, 1,2-diethoxyethane, 2-methyl tetrahydrofuran, methyl cyclopentyl ether; halogenated solvent such as dichloromethane, chloroform; $C_{6-14}$ aromatic hydrocarbon such as toluene, xylene, ethylbenzene and the like or mixture thereof. Preferably, reaction can be carried out at a temperature of −10 to 50° C. for 24 hours, more preferably till completion of the reaction. Reaction completion can be monitored by suitable techniques such as HPLC, TLC, GC or UPLC and the like. After the completion of reaction, reaction can be quenched with a suitable quenching agent, wherever required. Quenching agent can be selected from aqueous ammonium chloride, aqueous or concentrated hydrochloric acid, aqueous or concentrated hydrobromic acid, ammonium bromide and the like.

Compound of formula IV can be isolated from the reaction mixture using suitable conventional methods or can be used in situ for the further dehydration reaction. Compound of formula IV can be isolated from the reaction mixture by extraction with a suitable solvent followed by solvent removal from the organic layer. Suitable solvent used for the extraction includes halogenated solvent such as dichloromethane; aliphatic or aromatic hydrocarbon such as toluene, xylene, ethylbenzene; ether such as methyl tertiary butyl ether, isopropyl ether, 2-methyl tetrahydrofuran, methyl cyclopentyl ether and the like or mixture thereof. Compound of formula IV can be isolated from the resulting organic layer by removal of solvent using suitable techniques such as evaporation, distillation and the like.

Compound of formula III (which includes any of the isomers such as (S), (R) isomer or mixture thereof in any proportion) can be used for Grignard reaction which yields the corresponding isomer of hydroxyl compound of formula IV. As the reaction of compound of formula III under Grignard reaction conditions introduces a second asymmetric carbon atom, so compound of formula IV prepared by the process may include specific isomers such as (R)(R), (R)(S), (S)(S), (S)(R) or mixture of two or more in any proportion. Preferably, compound of formula IIIa can be reacted with a suitable reagent under Grignard reaction condition to form compound of formula IVa (which may have stereochemistry (R) or (S) at tertiary carbon, to which hydroxyl group is attached, or mixture thereof in any proportion).

Specific isomer or racemate of compound of formula IV, thus obtained, can be optionally purified employing suitable purification method such as acid base treatment, salt formation, crystallization and the like. Specifically, compound of formula IV can be purified by salt formation to enhance the chiral and/or chemical purity. The compound of formula IV can be reacted with a suitable acid followed by neutralization to form purified compound of formula IV or salt of compound of formula IV can be used for further reaction. Acid used for the salt formation can be selected from achiral acid which includes inorganic acid such as hydrochloric acid, sulfuric acid, nitric acid, phosphoric acid, perchloric acid; organic acid such as formic acid; acetic acid and the like or chiral acid such as camphor sulfonic acid, mandelic acid, substituted or unsubstituted tartaric acid and the like. Hydrochloric acid can be used as dilute (aqueous), concentrated hydrochloric acid, gaseous hydrogen chloride, solvent purged with hydrogen chloride or solvent in mixture with solvent. Solvent selected from alcohol, ethers, esters, nitriles, aliphatic or aromatic hydrocarbon, ketones, halogenated solvent and the like or mixture thereof. Similarly other acid employed for the salt formation can be used as such, aqueous solution, concentrated, gaseous form, or in mixture with a suitable solvent. Salt formation can be carried out in the presence of solvent selected from but not limited to alcohol such as methanol, ketone such as acetone; nitriles such as acetonitrile; ester such as ethyl acetate and the like or mixture thereof. Resulting salt of compound of formula IV can be neutralized with a suitable base to form purified compound of formula IV or salt of compound of formula IV can be used for the further reaction. Suitable base employed for the neutralization reaction includes organic base such as primary, secondary or tertiary amine; or inorganic base such as alkali or alkaline metal hydroxide, carbonate, bicarbonates, hydrides, alkoxides thereof. Purified compound of formula IV can be isolated from the reaction mixture using a suitable method known in the art.

Alternatively, compound of formula IV or salts thereof can be purified by crystallization or stirring in a suitable solvent.

Generally, purification process involved treating a compound of formula IV or salt thereof in a suitable solvent at a temperature of −20° C. to reflux temperature of solvent for 1 to 48 hours, at a temperature of −20 to 130° C. Suitable solvent includes $C_{5-14}$ aliphatic or aromatic hydrocarbons such as cyclohexane, toluene; ester such as ethyl acetate, propyl acetate; halogenated solvent such as dichloromethane, chloroform; ether such as methyl tertiary butyl ether, isopropyl ether and the like or mixture thereof. Purified compound of formula IV or salts thereof can be isolated from the reaction mixture by suitable methods. Preferably compound of formula IV or salts thereof can be isolated from using suitable techniques known in the art.

Compound of formula IV or salt thereof (including (R)(R), (R)(S), (S)(S) or (S)(R) isomer or mixture of two or more in any proportion) is then dehydrated to form corresponding diastereomer of alkene compound of formula V.

Generally, process involves the reaction of hydroxyl compound of formula IV or salts thereof with a suitable dehydrating agent at a temperature of −20 to 180° C. for 1 hour to 48 hours. Suitable dehydrating agent used for the reaction can be selected from the reagent known in the art that can effectively serve the purpose of removal of tertiary hydroxyl group. Specifically dehydrating agent can be selected from organic acid such as oxalic acid, terphthalic acid, citric acid and the like; inorganic acid such as hydrochloric acid, sulfuric acid, hydroiodic acid, hydrobromic acid, phosphoric acid, polyphosphoric acid, boric acid; sulfonic acid such as p-toluenesulfonic acid, benzenesulfonic acid, methanesulfonic acid and the like; alkali or alkaline metal sulfate such as sodium hydrogen sulfate, potassium hydrogen sulfate; pyridine complexes such as thionyl chloride pyridine complex, phosphorus oxychloride pyridine complex, methanesulfonyl chloride pyridine complex, trifluoroacetic anhydride dimethyl amino pyridine complex, silica, alumina, titanium oxide, niobium pentoxide; or acid catalyst such as ion exchange, nafion, amberlyst, zeolites, heteropolyacids, mixed metal oxides and the like. Acid employed for the reaction can be used as aqueous, gaseous or in mixture with organic solvent selected from alcohol, ethers, esters, nitriles, aliphatic or aromatic hydrocarbon, ketones, halogenated solvent and the like or mixture thereof. The reaction can be carried out in the presence or absence of a suitable solvent such as water, alcohol such as methanol, ethanol, isopropanol; $C_{3-12}$ ester such as ethyl acetate, methyl acetate, isopropyl acetate; $C_{4-14}$ ethers such as isopropyl ether, methyl tertiary butyl ether, 1,2-dimethoxy ethane, dioxane, 2-methyl tetrahydrofuran, cyclopentylmethyl ether; nitriles such as acetonitrile, propionitrile; aliphatic or $C_{6-14}$ aromatic hydrocarbon such as toluene, xylene, ethylbenzene; $C_{3-10}$ ketone such as acetone, methyl ethyl ketone, methyl isobutyl ketone; halogenated solvent such as dichloromethane, chloroform and the like or mixture thereof. After completion of the dehydration reaction, alkene compound of formula V can be isolated from the reaction mixture by suitable conventional method or can be in situ proceeded for further hydrogenation reaction.

Compound of formula V can be optionally isolated from the reaction mixture by addition of a suitable base followed by extraction of product with a suitable solvent. Suitable base used can be organic base or inorganic base. Organic base can be selected from amine of general formula NR'R"R'" (wherein R', R" and R'" are as defined above) such as trialkylamine and the like. Inorganic base can be selected from alkali or alkaline metal hydroxide, carbonates, bicarbonate, hydride or alkoxides thereof such as lithium carbonate, sodium carbonate, potassium carbonate, lithium hydroxide, potassium hydroxide, sodium hydroxide, lithium bicarbonate, sodium bicarbonate, potassium bicarbonate and the like or combination thereof. Suitable solvent employed for the extraction includes ester such as ethyl acetate; ethers such as methyl tertiary butyl ether, isopropyl ether, 2-methyl tetrahydrofuran; aliphatic or aromatic hydrocarbon such as toluene, xylene, cyclohexane and the like or mixture thereof. Organic layer can be optionally washed with water and/or brine. Compound of formula V can be recovered from the resulting solution by the removal of solvent using suitable techniques such as distillation, evaporation and the like.

The specific isomer of hydroxyl compound of formula IV (which includes any of the isomers such as (R)(R), (R)(S), (S)(S), (S)(R) isomer or mixture of two or more in any proportion) can be used for dehydration reaction which yields the corresponding isomer of alkene compound of formula V (which includes any of the isomers such as (Z)(R), (Z)(S), (E)(R) or (E)(S) isomer or mixture of two or more in any proportion). Preferably, compound of formula IVa can be reacted with a suitable dehydrating agent to form compound of formula Va (which includes any of the isomers such as (Z)(R), or (E)(R) which may or may not contain isomeric impurities).

Thereafter, alkene compound of formula V (which includes any of the isomers such as (Z)(R), (Z)(S), (E)(R) or (E)(S) isomer or mixture of two or more in any proportion) can be hydrogenated to form corresponding isomer of compound of formula VI.

Generally, process involves the reaction of compound of formula V with a suitable hydrogenating agent at a temperature of 0° C. to 180° C. for few minutes to several hours, preferably till completion of the reaction. The reagent employed for the reaction can be selected from the hydrogenating reagents known in the art that can be effectively serve the purpose provided it may not effect other functionality present in the compound. The reaction can be carried out by hydrogenation using hydrogen source such as nascent hydrogen in the presence of a suitable catalyst that includes but not limited to transition metal catalyst such as nickel (such as Raney nickel), palladium, platinum, ruthenium or rhodium and the like with or without support (carbon) or as organometallic complexes; or platinum oxide and the like. The presence or absence of solvent in the reaction mixture is not critical. The reaction can be carried out using heterogeneous or homogeneous chiral or achiral catalyst such as 2,2'-bis (diphenylphosphino)-1,1'-binaphthyl; 2,2'-bis(di-p-tolylphosphino)-1,1'-binaphthyl and the like. Hydrogen pressure applied during the reaction can be 1 to 10 kg/cm$^2$, preferably 3 to 8 kg/cm$^2$. The solvent employed for the reaction includes but not limited to $C_{1-10}$ alcohols such as methanol, ethanol, isopropanol; aliphatic or aromatic hydrocarbon such as toluene, xylene, ethylbenzene; $C_{3-10}$ esters such as ethyl acetate; nitrile such as acetonitrile; $C_{4-15}$ ethers such as methyl tertiary butyl ether, isopropyl ether, tetrahydrofuran, 2-methyl tetrahydrofuran, dioxane, 1,2-dimethoxy ethane, 1,2-diethoxy ethane; halogenated solvents such as dichloromethane; ketone such as acetone; acid such as formic acid, acetic acid and the like or mixture thereof. The reaction can optionally further carried out in the presence of suitable acid such as hydrochloric acid, hydrobromic acid; alkyl or aryl sulfonic acid such as methane sulfonic acid, p-toluenesulfonic acid; phosphoric acid, perchloric acid and the like or combination thereof. Usually, reaction is carried out at temperature of 20 to 50° C. for 48 hours, preferably till the completion of reaction. After completion of the reaction, reaction mixture can be filtered off to remove the catalyst. The compound of formula VI can be isolated from the reaction mixture by any conventional method or can be used as such for the further reaction.

Specifically, the compound of formula VI can be isolated from the reaction by removing solvent from the reaction mixture followed by neutralization of the reaction mixture and extraction of the resulting compound with a suitable solvent. Suitable base can be added to the reaction mass for the purpose of neutralization. Suitable base used can be organic base or inorganic base. Organic base can be selected from amine of general formula NR'R"R'" (wherein R', R" and R" are as defined above) such as ammonia, monoalkylamine, dialkylamine, trialkylamine and the like. Inorganic base can be selected from alkali or alkaline metal hydroxide, carbonates, bicarbonate, hydride or alkoxide thereof such as sodium carbonate, lithium carbonate, potassium carbonate, lithium hydroxide, potassium hydroxide, sodium hydroxide, sodium bicarbonate, potassium bicarbonate, lithium bicarbonate and the like. It is preferable to add water to the reaction mixture followed by washing with a suitable solvent prior to neutralization. The reaction mixture can be optionally saturated with alkali or alkaline metal halide such as sodium chloride and the like. Suitable solvent employed for the washing and/or extraction includes ester such as ethyl acetate; ethers such as diethyl ether, isopropyl ether; halogenated solvent such as dichloromethane, chloroform; aliphatic or aromatic hydrocarbon solvents such as toluene, xylene, ethylbenzene and the like or mixture thereof. Organic layer can be optionally washed with water and/or brine solution. Compound of formula VI can be recovered from the resulting solution by the removal of solvent using suitable techniques such as distillation, evaporation and the like.

Compound of formula V (which includes any of the isomers such as (Z)(R), (Z)(S), (E)(S), (E)(R) isomer or mixture of two or more in any proportion) used for hydrogenation reaction yields the corresponding isomer of compound of formula VI (which includes any of the isomers such as (R)(R), (R)(S), (S)(S), (S)(R) isomer or mixture of two or more in any proportion). Specifically, compound of formula Va (which includes any of the isomers such as (Z)(R), or (E)(R) or mixture thereof in any proportion) can be hydrogenated to form compound of formula VI (which includes any of the isomers such as (R)(R), or (S)(R) or mixture thereof in any proportion). Preferably the compound of formula Va can be reduced to give compound of formula VIa [(R)(R) isomer], in maximum proportion along with other isomers such as (S)(R) isomer in minimum amount. The ratio of compound of formula VIa i.e. (R)(R) isomer to corresponding (S)(R) isomer can vary from 70:30 to 99:1, preferably 80:20, more preferably 85:15, most preferably 90:10.

Compound of formula VI (including (R)(R), (R)(S), (S)(S), (S)(R) isomer or mixture of two or more in any proportion) can be purified to enhance the enantiomeric excess and/or diastereomeric excess by any suitable purification method such as salt formation, chromatographic purification, crystallization, distillation and the like. Specifically, compound of formula VI can be purified by salt formation to enhance the chemical and/or chiral purity and/or to minimize the impurities. The compound of formula VI can be reacted with a suitable acid followed by neutralization to form purified compound of formula VI. Acid used for the salt formation can be selected from achiral acid which includes inorganic acid such as hydrochloric acid, sulfuric acid, nitric acid, phosphoric acid, hypochloric acid; organic acid which includes $C_{1-20}$ carboxylic acid such as oxalic acid, formic acid, acetic acid and the like or chiral acid such as camphor sulfonic acid, mandelic acid, substituted or unsubstituted tartaric acid and the like. Resulting salt can be neutralized with a suitable base as defined above to form purified compound of formula VI.

Compound of formula VI or isomers can be treated with a suitable base to deprotect hydroxyl functionality to form corresponding isomer of compound of formula I or pharmaceutically acceptable salts thereof.

Generally, process involves the reaction of compound of formula VI with a suitable deprotecting reagent at a temperature of −10 to 180° C. for 48 hours. Deprotection reaction involves the removal of $R_1$ group by any suitable reagent known in the art for the deprotection of hydroxyl protecting group depending upon the nature of protecting group that effectively serve the purpose and are well known in the field of organic synthesis. Preferably deprotection reaction can be carried in the presence of a suitable base. Suitable base employed for the reaction can be organic or inorganic base. Organic base used for the reaction can be amine of general formula NR'R"R'" (wherein R', R" and R'" are as defined above) such as triethylamine, diisopropylethylamine, and the like. Inorganic base can be selected from alkali or alkaline metal hydroxide, carbonates, bicarbonate, hydride or alkoxide thereof such as sodium carbonate, lithium carbonate, potassium carbonate, lithium hydroxide, potassium hydroxide, sodium hydroxide, sodium bicarbonate, potassium bicarbonate, lithium bicarbonate and the like or combination thereof. The reaction can be carried out using a suitable solvent which includes water, $C_{1-10}$ alcohol such as methanol; aliphatic or aromatic hydrocarbon solvent, $C_{4-10}$ ether, nitriles, ketones, esters, halogenated solvents and the like or mixture thereof. The reaction can take place over a wide range of temperature depending upon the nature of $R_1$ group as well as on deprotecting reagent employed for the reaction. Usually reaction can be carried out at a temperature of 0 to 180° C. for 1 to 48 hours, preferably till the completion of the reaction. The reaction completion can be monitored by suitable techniques such as HPLC, TLC, GC or UPLC and the like. After the completion of the reaction, the desired product of formula I can be isolated from the reaction mixture using suitable conventional methods or can be converted in situ to pharmaceutically acceptable salts thereof.

Specifically, compound of formula I can be optionally isolated from the reaction mixture by the solvent removal followed by addition of water and water immiscible solvent to create a biphasic system. Suitable water immiscible solvent includes halogenated solvent such as dichloromethane, chloroform; $C_{4-14}$ ether such as isopropyl ether, methyl tertiary butyl ether, 1,2-dimethoxy ethane, dioxane, 2-methyl tetrahydrofuran, cyclopentylmethyl ether; $C_{6-14}$ aromatic hydrocarbon such as toluene, xylene, ethylbenzene; and the like or mixture thereof. Compound of formula I can be recovered from the resulting aqueous layer by its neutralization using suitable acid followed by extraction with a suitable solvent. Suitable acid includes inorganic acid such as hydrochloric acid, hydrobromic acid, sulfuric acid, phosphoric acid, nitric acid, hypochloric acid; organic acid such as $C_{1-20}$ carboxylic acid like formic acid, acetic acid etc. Suitable solvent employed for the extraction is selected from the solvent as described above. Compound of formula I can be isolated from the resulting organic layer by the removal of the solvent by distillation, evaporation and the like.

Similarly, the intermediate of formula VI (which includes any of the isomers such as (S)(S), (R)(R), (S)(R), (R)(S) or mixture of two or more in any proportion) can be deprotected using same reagents and reaction conditions as described above to yield corresponding compound of formula I (which includes any of the isomers such as (S)(S), (R)(R), (S)(R), (R)(S) or mixture of two or more in any proportion) or pharmaceutically acceptable salts thereof.

Preferably, compound of formula VIa [(R)(R) isomer] can be deprotected to produce tapentadol of formula Ia or pharmaceutically acceptable salts thereof. More preferably, compound of formula VIa can be deprotected to produce tapentadol hydrochloride.

Accordingly, the present invention includes all possible stereoisomers of compound of formula I as well as of intermediates. It also includes not only racemic compounds, or racemic mixtures thereof, but also optically active isomers as well. When a compound of formula I or its intermediate is desired as a single enantiomer or diastereomer, it may be obtained either by resolution of the corresponding racemic product or by a stereospecific synthesis from either optically pure starting material or any convenient intermediate. Where stereospecific synthesis techniques are employed or optically active compounds are employed as starting materials, individual isomers may be prepared directly; on the other hand, if a mixture of isomers is prepared, the individual isomers may be obtained by conventional resolution techniques known in the literature. Therefore, resolution of any of the intermediate during synthesis can be carried out and proceeded to form specific isomer of 1-phenyl-3-dimethylaminopropane derivatives of formula I, preferably tapentadol of formula Ia.

The present invention provides that tapentadol of formula Ia can be prepared either by employing chiral synthesis using specific isomer of the intermediate or by performing resolution at the final stage. When 1-phenyl-3-dimethylaminopropane derivatives of formula I prepared by the process of present invention is racemic then it can be converted to tapentadol of formula Ia by the resolution of racemic product.

Generally, resolution is achieved by recrystalliztion. Process comprises dissolving racemic mixture in a suitable solvent and addition of a suitable resolving agent. Suitable solvent can be selected on the basis whether diastereomeric salt precipitates out differently. The separation may result simply by stirring at a suitable temperature in a solvent until one of the salts preferentially precipitate out.

Purification of diastereomeric salt is possible by refluxing in a suitable solvent. Preferably, water, alcohols, ethers, ketones, halogenated solvents, esters, nitriles, aprotic solvents such as N,N-dimethylformamide, dimethylsulfoxide, N-methylpyrrolidinone and the like or mixture thereof. Thereafter, free base can be liberated from its salt using a suitable base. The diastereomeric salt is dissolved or suspended in a mixture of water and organic solvent and is neutralized with a base under stirring, the free base is obtained after separation of aqueous layer and evaporation of the organic solvent.

Suitable base for hydrolysis of diastereomeric salt includes alkali (lithium, sodium or potassium and the like) or alkaline metal (calcium, magnesium and the like) hydroxides, carbonates, bicarbonates, hydride and alkoxides thereof in aqueous medium at temperature varying between −20 to 150° C. The solvents used during the resolution includes but not limited to water, ethers, esters, ketones, halogenated solvents, nitrile, aliphatic or aromatic hydrocarbons and the like or mixture thereof. The resolution can be accomplished at temperature from −20° C. to 150° C. or reflux temperature of the solvent used. Suitable resolving agent employed can be acid chiral reagents that include diaroyl acid such as dibenzoyl tartaric acid; camphor sulfonic acid, mandelic acid and the like or any other reagent suitable for the chiral separation, known in the art.

These terms and methods for identifying and selecting the desired compounds are well known in the art for example, diastereoisomers may be separated by physical separation methods such as fractional crystallization and chromatographic techniques, and enantiomers may be separated from each other by the selective crystallization of the diastereomeric salts with optically active acids or bases. Pure stereoisomer may also be prepared synthetically from the appropriate stereochemically pure starting materials, or by using stereoselective reactions.

Compound of formula I prepared by the process of present invention can be converted, in a known manner, into acid addition salts with physiologically acceptable acids, for example hydrochloric acid, hydrobromic acid, sulfuric acid, phosphoric acid, methanesulfonic acid, formic acid, acetic acid, levulinic acid, oxalic acid, succinic acid, tartaric acid, mandelic acid, fumaric acid, lactic acid, citric acid, glutamic acid and/or aspartic acid, stearic acid or palmitic acid, orotic acid and the like. Salt formation is preferably effected in a solvent that includes water, ether such as diethyl ether, diisopropyl ether; ester such as alkyl acetates or propionates; ketone such as acetone and/or 2-butanone, methyl iso-butyl ketone; alcohol, aliphatic or aromatic hydrocarbon; halogenated solvents such as dichloromethane, nitriles; or dimethylsulfoxide, dimethylformamide, dimethylacetamide, N-methylpyrrolidone, sulfolane and the like or mixture thereof. Preferably tapentadol hydrochloride is prepared.

In another alternate way, pharmaceutically acceptable salt of compound of formula I can be prepared directly from intermediate of formula VI by in situ formation of free base of compound of formula I. Specifically, tapentadol of formula Ia can be converted to tapentadol hydrochloride using a suitable source of hydrochloric acid. The process involves the reaction of tapentadol in a suitable solvent with a source of hydrochloric acid at a temperature of −20 to 80° C. for 15 minutes to several hours, preferably till the salt formation. Source of hydrochloric acid employed for the reaction can be aqueous, concentrated hydrochloric acid, gaseous hydrogen chloride, solvent purged with hydrogen chloride gas or hydrochloric acid in solution with a solvent. Solvent used for the generation of source of hydrochloric acid can be selected from $C_{1-10}$ alcohol such as methanol; $C_{4-14}$ ether such as isopropyl ether; $C_{3-10}$ ester such as ethyl acetate and the like or mixture thereof. Solvent employed for the salt formation reaction can be selected from halogenated solvent such as dichloromethane, chloroform; nitrile such as acetonitrile; ether such as tetrahydrofuran; alcohol such as methanol; ketone such as acetone and the like or mixture thereof. After the completion of the salt formation, tapentadol hydrochloride can be isolated from reaction mixture by the suitable techniques such as solvent removal by evaporation, distillation and the like.

Compound of formula I or tapentadol or pharmaceutically acceptable salt thereof thus isolated can be purified using a suitable purification method such as crystallization, slurry wash, washing or acid base treatment, refluxing. Suitable solvent employed for the purification includes water, alcohol such as isopropanol, ester such as ethyl acetate; nitriles, ethers such as isopropyl ether, aprotic solvent, ketones such as acetone, aliphatic or aromatic hydrocarbon solvents, halogenated solvents and the like or mixture thereof.

Specifically, tapentadol hydrochloride can be purified to enhance the enantiomeric purity or to minimize the other impurities in final product. It can be purified by crystallization or slurry wash in a suitable solvent. Preferably, tapentadol hydrochloride can be stirred in a suitable solvent at a temperature of −10 to 80° C. for 15 minutes to several hours. Suitable solvent includes but not limited to alcohol such as methanol, isopropanol; ester such as ethyl acetate; ketone such as acetone, methyl ethyl ketone; ether such as methyl tert-butyl ether, tetrahydrofuran, isopropyl ether, 2-methyl tetrahydrofuran, 1,4-dioxane; halogenated solvent such as dichloromethane; nitriles such as acetonitrile, propionitrile and the like or mixture thereof. Thereafter, mixture can be cooled to a temperature of −30° C. to ambient temperature. Purified final product can be isolated from the mixture by using suitable techniques known in the art such as filtration, centrifugation and the like.

Purification process can be repeated till the desired chemical as well as chiral purity of the final product is achieved.

Purification of tapentadol of formula Ia or pharmaceutically acceptable salts thereof can be repeated with same or different solvent till the desired optical purity is achieved.

Tapentadol hydrochloride obtained by the process of present invention having high enantiomeric excess, preferably more than 99%, more preferably 100% ee.

The starting compound i.e. 1-(3-hydroxy-phenyl)-propan-1-one as used in the present invention can be prepared by the methods known in the art or can be procured from the commercial source.

Intermediates described here in the present invention may be optionally purified to enhance the purity of the product.

Any suitable purification procedure such as, for example, crystallization, derivatisation, slurry wash, salt preparation, various chromatographic techniques, solvent anti-solvent system or combination of these procedures, may be employed to get the purified material. However, other equivalent procedures such as acid-base treatment or acid-acid treatment could, also be used, to purify the intermediates as well as final product. The solvents used for the purification of final compound may be selected amongst water, $C_{1-6}$ alcohols, aliphatic $C_{3-6}$ ketones, $C_{5-10}$ aliphatic or $C_{5-12}$ aromatic hydrocarbons, $C_{3-12}$ aliphatic esters, $C_{3-6}$ ethers, nitrile, halogenated solvents such as chloroform, dichloromethane, aprotic solvents such as N,N-dimethylformamide, dimethylsulfoxide, dimethylacetamide, N-methylpyrrolidinone, sulfolane and the like or mixtures thereof in suitable proportion.

As used herein the term "conventional methods for the isolation of intermediates as well as final product" may be varied depending upon the nature of the reactions, nature product of the reaction, medium of the reaction and the like. the suitable conventional methods can be selected amongst but not limited to distillation of the solvent, addition of water to the reaction mixture followed by extraction with water immiscible solvents, removal of the insoluble particles from the reaction mixture, if present, by filtration or centrifugation or by decantation, addition of water immiscible organic solvent, addition of a solvent to the reaction mixture which precipitate the product, neutralizing the reaction mixture with a suitable acid or base whichever is applicable.

The order and manner of combining the reactants at any stage of the process are not critical and may be varied. The reactants may be added to the reaction mixture as solids, or may be dissolved individually and combined as solutions. Further, any of the reactants may be dissolved together as sub-groups, and those solutions may be combined in any order. The time required for the completion of the reaction may also vary widely, depending on many factors, notably the reaction temperature and the nature of the reagents and solvents employed. Wherever required, progress of the reaction may be monitored by suitable chromatographic techniques such as High performance liquid chromatography (HPLC), gas chromatography (GC), ultra pressure liquid chromatography (UPLC) or thin layer chromatography (TLC).

The major advantage of present invention is to provide an efficient and industrially advantageous process for preparation of 1-phenyl-3-dimethylaminopropane derivatives of formula I, preferably tapentadol or salts thereof using novel intermediates. Process of the present invention is further advantageous as product obtained after hydrogenation of alkene compound of formula Va is mainly compound of formula VIa [i.e. (R)(R) isomer] contaminated with minor amount of other isomers like (S)(R) isomer, which can be removed during reaction workup and further course of reaction.

Compound of formula VIa contaminated with undesired (S)(R) isomer about 2 to 20% yields tapentadol of formula Ia or pharmaceutically acceptable salts having undesired isomer in minimum amount, less than 4%, preferably less than 1%, more preferably free from the undesired isomer. Undesired isomer of tapentadol removed during the reaction and workup and/or by simple purification or crystallization. Main advantage of the present invention is that it yield tapentadol hydrochloride with high enantiomeric excess, preferably more than 99% ee, more preferably 100% ee. Further, the present invention also provides novel intermediates, which are useful in the preparation of the tapentadol and its pharmaceutically salts thereof.

Although, the following examples illustrate the practice of the present invention in some of its embodiments, the examples should not be construed as limiting the scope of the invention. Other embodiments will be apparent to one skilled in the art from consideration of specification and examples.

EXAMPLES

Example 1

Preparation of Toluene-4-sulfonic Acid 3-propionyl-phenyl Ester

To a stirred suspension of 1-(3-hydroxy-phenyl)-propan-1-one (200 g, 1.33 mol) and potassium carbonate (368 g, 2.66 mol) in dichloromethane (2 L), p-toluenesulfonyl chloride (279.62 g, 1.46 mol) was added at 0° C. and stirred at 30-35° C. for 1 hour. Reaction mixture was diluted with dichloromethane (1 L) and washed with water (2×1 L). Organic layer was separated and dried.

Solvent were distilled off to give 405 g of the title compound.

By using the similar method, 85 g of the toluene-4-sulfonic acid 3-propionyl-phenyl ester was prepared from 50 g of 1-(3-hydroxy-phenyl)-propan-1-one by replacing potassium carbonate with sodium hydroxide and replacing dichloromethane with toluene.

$^1$H NMR δ (CDCl$_3$): 7.19-7.85 (m, 8H, ArH), 2.9 (2H, q, CH$_2$CH$_3$), 2.45 (3H, s, ArCH$_3$), 1.17 (3H, t, CH$_2$CH$_3$)

Example 2

Preparation of Toluene-4-sulfonic Acid 3-propionyl-phenyl Ester

To a stirred suspension of 1-(3-hydroxy-phenyl)-propan-1-one (2 kg, 13.32 mol) and potassium carbonate (3.681 kg, 26.64 mol) in dichloromethane (20 L), p-toluenesulfonyl chloride (2.8 kg, 14.65 mol) was added at 30-35° C. The reaction mixture was stirred at 30-35° C. for 1 hour. Reaction mixture was diluted with dichloromethane (10 L) and washed with water (2×10 L). Dichloromethane layer separated, dried and solvent distilled off to give title compound. Cyclohexane (10 L) was added to the resulting product at 65-70° C. and stirred for 2 hours. Mixture was cooled to ambient temperature, filtered and dried to give 3.87 kg the title compound.

Product displays the $^1$H-NMR spectrum similar to product of example 1.

Example 3

Preparation of [2RS]-3-dimethylamino-1-(3-hydroxy-phenyl)-2-methyl-propan-1-one

A mixture of 1-(3-hydroxy-phenyl)-propan-1-one (5 g, 0.03 mol), paraformaldehyde (1 g, 0.03 mol), dimethylamine hydrochloride (3 g, 0.04 mol), hydrochloric acid (3.4 ml, 30%) and isopropanol (15 ml) was refluxed for 16 hours. Isopropanol was distilled off from the reaction mixture and resulting reaction mass was cooled to 25-30° C. Water (15 ml) was added to the reaction mass and washed with isopropyl ether (2×15 ml). Layers were separated and aqueous layer was added to a stirred mixture of aqueous sodium hydroxide solution (1.2 g in 16 ml water) and methyl tert-butyl ether (25 ml). Layers were separated. Organic layer was washed with water (10 ml), dried and solvent was distilled to give 3.45 g of the title compound.

Example 4

Preparation of [2RS]-toluene-4-sulfonic Acid 3-(3-dimethylamino-2-methyl-propionyl)-phenyl Ester Method A:

A mixture of toluene-4-sulfonic acid 3-propionyl-phenyl ester (405 g, 1.33 mol), paraformaldehyde (100.1 g, 3.33 mol), dimethylamine hydrochloride (217.2 g, 2.66 mol), aqueous hydrochloric acid (32.5 ml, 30%) and isopropanol (1.22 L) was refluxed for 16 hours. Isopropanol was distilled off from the reaction mixture and reaction mass was cooled to 25-30° C. Water (1.62 L) was added to the reaction mass and washed with isopropyl ether (2×1.22 L). Resulting aqueous layer was added to a stirred mixture of aqueous sodium hydroxide solution (148.2 g in 148.2 ml of water) and methyl tertiary butyl ether (2.02 L). Organic layer was separated, washed with water (1 L), dried and solvent was distilled to give 397.5 g (82.6%) of the title compound having purity 41.49% of (S) isomer and 58.51% of (R)-isomer by chiral HPLC.

Method B:

A mixture of toluene-4-sulfonic acid 3-propionyl-phenyl ester (35 g, 0.12 mol), paraformaldehyde (8.7 g, 0.29 mol), dimethylamine hydrochloride (18.75 g, 0.230 mol), aqueous hydrochloric acid (2.8 ml, 30%) and isopropanol (88 ml) was refluxed for 12 hours. Reaction mixture was cooled to 25-30° C. followed by addition of water (105 ml) and cyclohexane (35 ml). Reaction mixture was stirred at ambient temperature and aqueous layer was separated. The aqueous layer was added to a stirred mixture of aqueous sodium hydroxide (12.8 g in 26 ml water) and methyl tertiary butyl ether (175 ml). The organic layer was separated, washed with water, dried and solvent was distilled to give 33 g of the title compound.

Method C:

A mixture of toluene-4-sulfonic acid 3-propionyl-phenyl ester (3.87 kg, 12.72 mol), paraformaldehyde (0.96 kg, 32 mol), dimethylamine hydrochloride (2.08 kg, 25.51 mol), aqueous hydrochloric acid (0.31 L, 30%) and isopropanol (11.61 L) was refluxed for 24 hours. Isopropanol was distilled off from the reaction mixture and thereafter mixture was cooled to 25-30° C. Water (15.5 L) was added to the reaction mixture and washed with isopropyl ether (2×12 L). Layers were separated and aqueous sodium carbonate (2.02 kg in 2.02 L demineralised water) was added to the aqueous layer. Mixture was extracted with dichloromethane (2×12 L). Sodium hydroxide (150 g) was added to remaining aqueous layer, dissolved by stirring and extracted with dichloromethane (2×6 L). Combine all dichloromethane extracts, washed with brine (1.35 kg in 13.5 L demineralised water). The dichloromethane layer was separated, dried and solvent was distilled off to give 4.22 kg of the title compound having purity 47.88% of (S) isomer and 52.12% of (R)-isomer by chiral HPLC.

Method D:

To a stirred suspension of 3-dimethylamino-1-(3-hydroxyphenyl)-2-methyl-propan-1-one (3 g, 0.01 mol) and potassium carbonate (4 g, 0.03 mol) in dichloromethane (30 ml), p-toluenesulfonyl chloride (3.04 g, 0.02 mol) was added at 30-35° C. and reaction mixture was stirred for 1 hour. Thereafter, mixture was diluted with dichloromethane (10 ml) at ambient temperature and washed with water (2×15 ml). Dichloromethane layer was separated, dried and solvent was distilled off to give 3.4 g of the title compound.

$^1$H NMR δ (CDCl$_3$): 7.23-7.88 (8H, m, ArH); 3.53 (1H, m, CHCH$_3$), 2.74 (1H, dd, NCH$_2$), 2.43 (3H, s, ArCH$_3$), 2.28 (1H, dd, NCH$_2$), 2.19 (6H, s, NCH$_3$), 1.11 (3H, d, CH$_3$CH); Mass analysis (m/e) shows M$^{+1}$ peak at 362.21.

Example 5

Preparation of L-dibenzoyl Tartaric Acid Salt of [2S]-toluene-4-sulfonic Acid 3-(3-dimethylamino-2-methyl-propionyl)-phenyl Ester To a stirred solution of L-dibenzoyl tartaric acid (4.15 kg, 11.58 mol) in ethyl acetate (33 L), a solution of [2RS]-toluene-4-sulfonic acid 3-(3-dimethylamino-2-methyl-propionyl)-phenyl ester (4.15 kg, 11.48 mol) in ethyl acetate (8.5 L) was added at 45-50° C. The mixture was stirred at 45-50° C. for 2 hours and then cooled to ambient temperature. Mixture was further stirred for 10 hours, filtered, washed with ethyl acetate (2 L) and dried to give 7.74 kg of the title compound having purity 94%; and (R)-isomer: 6% by chiral HPLC.

Example 6

Purification of L-dibenzoyl Tartaric Acid Salt of [2S]-toluene-4-sulfonic Acid 3-(3-dimethylamino-2-methyl-propionyl)-phenyl Ester L-dibenzoyl tartaric acid salt of [2S]-toluene-4-sulfonic acid 3-(3-dimethylamino-2-methyl-propionyl)-phenyl ester (7.6 kg, having purity 94%; and (R)-isomer: 6%) and ethyl acetate (34 L) were stirred at 45-50° C. for 2 hours. Mixture was then cooled to ambient temperature and further stirred for 10 hours. Resulting product was filtered, washed with ethyl acetate (2 L) and dried to give 7.4 kg of the title compound having purity 97.9%; and (R)-isomer: 2.1% by chiral HPLC.

$[α]_D^{RT}$=−48.37 (c=1%; methanol)

Example 7

Preparation of [2S]-toluene-4-sulfonic Acid 3-(3-dimethylamino-2-methyl-propionyl)-phenyl Ester To a stirred solution of sodium carbonate (3.33 kg, 31.42 mol) in demineralised water (22.2 L), L-dibenzoyl tartaric acid salt of [2S]-toluene-4-sulfonic acid 3-(3-dimethylamino-2-methyl-propionyl)-phenyl ester (7.4 kg) and dichloromethane (37 L) were added at ambient temperature and reaction mixture was stirred at 25-30° C. for 2 hours. Layers were separated. Dichloromethane layer was separated, and the aqueous layer was extracted with dichloromethane (22.2 L). All dichloromethane extracts were combined, washed with brine (7.4 L), separated, dried and solvent was distilled off to give 3.72 kg of the title compound having purity 97.9%; and (R)-isomer: 2.1% by chiral HPLC.

$^1$H NMR δ (CDCl$_3$): 7.23-7.87 (8H, m, ArH), 3.52 (1H, m, CHCH$_3$), 2.74 (1H, dd, NCH$_2$), 2.43 (3H, s, ArCH$_3$), 2.28 (1H, dd, NCH$_2$), 2.19 (6H, s, NCH$_3$), 1.11 (3H, d, CH$_3$CH); Mass analysis (m/e) shows M$^{+1}$ peak at 362.21;

$[α]_D^{RT}$+12.7 (c=1%; methanol)

Example 8

Preparation of [2RS]-toluene-4-sulfonic Acid 3-(3-dimethylamino-2-methyl-propionyl)-phenyl Ester To a solution of [2RS]-toluene-4-sulfonic acid 3-(3-dimethylamino-2-methyl-propionyl)-phenyl ester (397.5 g, 1.100 mol) in ethyl acetate (0.8 L), was added a solution of L-dibenzoyl tartaric acid (397.9 g, 1.057 mol) in ethyl acetate (1.2 L) at ambient temperature. The reaction mixture was cooled to 10-15° C. and stirred for 5 hours. Reaction mixture was filtered, washed with cold ethyl acetate (0.78 L) and dried to give 675 g of L-dibenzoyl tartarate salt of title compound. Mixture of resulting product, dichloromethane (8.1 L) and aqueous ammonia (1.7 L) were stirred at 20-25° C. for 1 hour. Dichloromethane layer was separated, washed with water (1.0 L), dried and solvent was distilled off to give 338 g (85%) of the title compound having purity 98%; and (R) isomer: 2% by chiral HPLC.

Product displays the $^1$H-NMR as well as Mass analysis results same as similar to product of example 7.

Example 9

Preparation of [2RS,3RS]-toluene-4-sulfonic Acid 3-(3-dimethylamino-1-ethyl-1-hydroxy-2-methyl-propyl)-phenyl Ester To a stirred solution of [2RS]-toluene-4-sulfonic acid 3-(3-dimethylamino-2-methyl-propionyl)-phenyl ester (15 g, 0.04 mol) in dry tetrahydrofuran (45 ml), a solution of ethyl magnesium chloride (7.37 g, 0.08 mol) in tetrahydrofuran (42 ml) was added at 25-30° C. and stirred for 3 hours. Reaction mixture was quenched with aqueous ammonium chloride (50 ml, 20%) followed by layer separation. Aqueous layer was extracted with dichloromethane (3×50 ml). All organic extracts were combined and solvent was distilled off from the organic layer. The residue was re-dissolved in dichloromethane (200 ml) at ambient temperature, washed with water, dried and solvent was distilled off to give 15.78 g of the title compound.

Example 10

Preparation of [2S,3RS]-toluene-4-sulfonic Acid 3-(3-dimethylamino-1-ethyl-1-hydroxy-2-methyl-propyl)-phenyl Ester Method A:
To [2S]-toluene-4-sulfonic acid 3-(3-dimethylamino-2-methyl-propionyl)-phenyl ester (235.6 g, 0.65 mol) in dry tetrahydrofuran (707 ml), ethyl magnesium chloride (260 g, 1.96 mol) in tetrahydrofuran (977 ml, 17.8%) was added at 25-30° C. and stirred for 3 hours. Reaction mixture was quenched with aqueous ammonium chloride (850 ml, 20%) followed by layer separation. Aqueous layer was extracted with methyl tertiary butyl ether (3×850 ml). All organic extracts were combined and distilled off to give a residue. Resulting residue was dissolved in methyl tert-butyl ether (1.2 L), washed with water (400 ml) and solvent was distilled off to give 248 g (97%) of the title compound having purity 97.42% and (R)-isomer: 2.58% by chiral HPLC.
Method B:
To a stirred solution of [2S]-toluene-4-sulfonic acid 3-(3-dimethylamino-2-methyl-propionyl)-phenyl ester (3.72 kg, 10.29 mol) in dry tetrahydrofuran (11.2 L), a solution of ethyl magnesium chloride in tetrahydrofuran (1.83 kg in 10.3 L, 20.58 mol) was added at 25-30° C. and stirred for 3 hours. Reaction mixture was quenched with aqueous ammonium chloride (37 L, 20%) followed by layer separation. Aqueous layer was extracted with toluene (3×15 L). All organic extracts were combined, washed with brine (10 L, 20%), separated, dried and distilled off to give 4.01 kg of the title compound having purity 97.2% and (R)-isomer: 2.8% by chiral HPLC.

By using the similar method, 15.16 g of [2S,3RS]-toluene-4-sulfonic acid 3-(3-dimethylamino-1-ethyl-1-hydroxy-2-methyl-propyl)-phenyl ester was prepared from 14 g of [2S]-toluene-4-sulfonic acid 3-(3-dimethylamino-2-methyl-propionyl)-phenyl ester and extraction was carried using dichloromethane in place of methyl tertiary butyl ether.

$^1$H NMR δ (CDCl$_3$): 6.92-7.69 (m, 8H, ArH), 2.42 (3H, s, ArCH$_3$), 2.21 (6H, s, NCH$_3$), 1.9 (5H, m, NCH$_2$CH & CH$_3$CH$_2$), 0.7 (3H, t, CH$_3$CH$_2$CH), 0.63 (3H, d, CHCH$_3$), 8.40 (1H, bs, OH)

Mass analysis (m/e) shows M$^{+1}$ peak at 392.10

Example 11

Preparation of [2S,3RS]-toluene-4-sulfonic Acid 3-(3-dimethylamino-1-ethyl-1-hydroxy-2-methyl-propyl)-phenyl Ester Hydrochloride To a solution of [2S,3RS]-toluene-4-sulfonic acid 3-(3-dimethylamino-1-ethyl-1-hydroxy-2-methyl-propyl)-phenyl ester (5 g, 0.01 mol) in methanol (10 ml), isopropyl ether hydrochloride (3.4 ml, 15%, 0.01 mol) was added at ambient temperature and stirred for 15 minutes. Solvents were distilled off from the mixture and residue was crystallized from ethyl acetate to give 4.2 g of title compound having purity 99.62% and (R)-isomer: 0.38% by chiral HPLC.

Example 12

Preparation of [1RS]-toluene-4-sulfonic Acid 3-[1-(2-dimethylamino-1-methyl-ethyl)-propenyl]-phenyl Ester A mixture of [2RS,3RS]-toluene-4-sulfonic acid 3-(3-dimethylamino-1-ethyl-1-hydroxy-2-methyl-propyl)-phenyl ester (50 g, 0.13 mol) and concentrated hydrochloric acid (250 ml) was refluxed for 24 hours. Excess hydrochloric acid was partially distilled off from the reaction mixture. Reaction mixture was cooled to 10-15° C. and basified with potassium carbonate (2 L, 20% aqueous). Resulting product was extracted with dichloromethane (3×μL). Organic layer was washed with water (500 ml), dried and solvent was distilled off to give 43.9 g of the title compound.

Mass analysis (m/e) shows M$^{+1}$ peak at 374.15

Example 13

Preparation of [1R]-toluene-4-sulfonic acid 3-[1-(2-dimethylamino-1-methyl-ethyl)-propenyl]-phenyl ester Method A:
A mixture of [2S,3RS]-toluene-4-sulfonic acid 3-(3-dimethylamino-1-ethyl-1-hydroxy-2-methyl-propyl)-phenyl ester (248 g, 0.633 mol) and concentrated hydrochloric acid (1.24 L) was refluxed for 24 hours. Hydrochloric acid was partially distilled off. The reaction mixture was basified with potassium carbonate (900 ml, 20% aqueous) at 10-15° C. Resulting product was extracted with ethyl acetate (3×1.25 L) and washed with water (1.25 L). Organic layer was dried and solvent was distilled off to give 228.35 g of title compound.

By using the similar method, 51 g of [1R]-toluene-4-sulfonic acid 3-[1-(2-dimethylamino-1-methyl-ethyl)-propenyl]-phenyl ester was prepared from 56 g of [2S,3RS]-toluene-4-sulfonic acid 3-(3-dimethylamino-1-ethyl-1-hydroxy-2-methyl-propyl)-phenyl ester by using sodium carbonate in place of potassium carbonate.
Method B:
A mixture of [2S,3RS]-toluene-4-sulfonic acid 3-(3-dimethyl amino-1-ethyl-1-hydroxy-2-methyl-propyl)-phenyl ester (10 g, 0.03 mol), toluene (50 ml) and polyphosphoric acid (20 g) was heated to 120° C. for 4 hours and then cooled to 0° C. Reaction mixture was quenched with water (30 ml), followed by addition of sodium carbonate (10 g). Resulting product was extracted with toluene (3×50 ml). All extracts were combined, washed with brine, dried and solvent were distilled off to give 8.1 g of the title compound.

Method C:

A mixture of [2S,3RS]-toluene-4-sulfonic acid 3-(3-dimethylamino-1-ethyl-1-hydroxy-2-methyl-propyl)-phenyl ester (3.97 kg, 10.14 mol) and concentrated hydrochloric (20 L) was refluxed for 24 hours and hydrochloric acid was partially distilled off. The reaction mixture was basified with potassium, carbonate (43 L, 20% aqueous) at 10-15° C. Resulting product was extracted with dichloromethane (3×15 L). Layers were separated. Dichloromethane layer was washed with brine (20 L, 20% aqueous), dried and solvent was distilled off to give 3.475 kg of the title compound.

Method D:

A mixture of [2S,3RS]-toluene-4-sulfonic acid 3-(3-dimethylamino-1-ethyl-1-hydroxy-2-methyl-propyl)-phenyl ester hydrochloride (5 g, 0.01 mol) and concentrated hydrochloric acid (25 ml) was refluxed for 24 hours and hydrochloric acid was partially distilled off. The reaction mixture was basified with potassium carbonate (18 ml, 20% aqueous) at 10-15° C. Resulting product was extracted with dichloromethane (3×30 ml). Dichloromethane was washed with water (20 ml), dried and solvent was distilled off to give 4.06 g of the title compound.

Mass analysis (m/e) shows $M^{+1}$ peak at 374.15.

Example 14

Preparation of [1RS,2RS]toluene-4-sulfonic Acid 3-(3-dimethylamino-1-ethyl-2-methyl-propyl)-phenyl Ester A mixture of [1RS]-toluene-4-sulfonic acid 3-[1-(2-dimethylamino-1-methyl-ethyl)-propenyl]-phenyl ester (10 g, 0.03 mol), ethanol (38 ml), concentrated hydrochloric acid (4.5 ml, 30%) and Pd/C (10%, 3 g) was hydrogenated at 5 kg/cm² for 10 hours. The reaction mixture was filtered through hyflo bed and the filtrate was distilled off to remove ethanol. Water (40 ml) was added to the resulting residue at ambient temperature and reaction mixture was washed with isopropyl ether (2×15 ml). Aqueous sodium carbonate (23 ml, 20%) was added to the reaction mixture till pH 7-8 and saturated with sodium chloride (3.5 g). Resulting product was extracted with dichloromethane (3×50 ml). All organic extracts were combined, washed with brine, dried and solvent distilled off to give 9.8 g of the title compound.

Mass analysis (m/e) shows, $M^{+1}$ peak at 376.15

Example 15

Preparation of [1R,2R]toluene-4-sulfonic Acid 3-(3-dimethylamino-1-ethyl-2-methyl-propyl)-phenyl Ester Method A:

A mixture of [1R]-toluene-4-sulfonic acid 3-[1-(2-dimethylamino-1-methyl-ethyl)-propenyl]-phenyl ester (36 g, 0.10 mol), ethanol (360 ml), methanesulfonic acid (10.18 g, 0.106 ml) and Pd/C (10%, 10.8 g) was hydrogenated at 5 kg/cm² for 36 hours in a parr shaker. The reaction mixture was filtered off through hyflow bed and the filtrate was distilled off to remove ethanol. Water (180 ml) was added to the reaction mixture at ambient temperature followed by addition of aqueous sodium carbonate (160 ml, 15%) till pH 7-8 and reaction mixture was saturated with sodium chloride (40 g). The product was extracted with ethyl acetate (3×180 ml) and washed with water (180 ml). Organic layer was dried and solvent was distilled off to give 31 g (85.7%) of title compound.

Method B:

A mixture of [1R]-toluene-4-sulfonic acid 3-[1-(2-dimethylamino-1-methyl-ethyl)-propenyl]-phenyl ester (100 g, 0.27 mol), ethanol (1.0 L), concentrated hydrochloric acid (45 ml) and Pd/C (10%, 30 g) was hydrogenated at 6 kg/cm² for 36 hours in a parr shaker. The reaction mixture was filtered off through hyflow bed and filtrate was distilled off to remove ethanol. Water (500 ml) was added to the reaction mixture at ambient temperature and the reaction mixture was washed with isopropyl ether (2×300 ml). Aqueous sodium carbonate (450 ml, 15%) was added to the resulting reaction mixture till pH 7-8 and saturated with sodium chloride (112 g). The product was extracted with ethyl acetate (3×500 ml) and washed with water (500 ml). Organic layer was dried and solvent was distilled off to give 88.9 g (88.4%) of title compound.

Method C:

A mixture of [1R]-toluene-4-sulfonic acid 3-[1-(2-dimethylamino-1-methyl-ethyl)-propenyl]-phenyl ester (3 kg, 8.03 mol), ethanol (30 L), concentrated hydrochloric acid (1.35 L, 30%) and Pd/C (10%, 900 g) was hydrogenated at 5 kg/cm² for 10 hours in a hydrogenation unit. The reaction mixture was filtered off through hyflow bed and filtrate was distilled off to remove ethanol. Water (6 L) was added to the reaction mixture and the reaction mixture was washed with isopropyl ether (2×2 L). Sodium carbonate (7 L, 20%) was added to the reaction mixture till pH 7-8 and saturated with sodium chloride (1 kg). The product was extracted with dichloromethane (3×15 L) and all extracts were combined. Organic layer was washed with brine, dried and solvent was distilled off to give 3.01 kg of the title compound.

$^1$H NMR δ (CDCl$_3$): 6.66-7.65 (8H, m, ArH), 2.41 (3H, s, ArCH$_3$), 2.30 (1H, m, CHCH$_2$CH$_3$), 2.09 (6H, s, CH, NCH$_3$), 1.89 (2H, s, NCH$_2$), 1.71 (2H, m, CH$_2$CH$_3$), 1.42 (1H, m, CH$_3$CH), 0.84 (3H, d, CH$_3$CH); 0.59 (3H, t, CH$_3$CH$_2$)

Mass analysis (m/e) shows $M^{+1}$ peak at 376.15

Example 16

Preparation of [1R,2R]toluene-4-sulfonic Acid 3-(3-dimethylamino-1-ethyl-2-methyl-propyl)-phenyl Ester Step I: Preparation of [1R,2R]toluene-4-sulfonic Acid 3-(3-dimethylamino-1-ethyl-2-methyl-propyl)-phenyl Ester Oxalate To a solution of [1R,2R]toluene-4-sulfonic acid 3-(3-dimethylamino-1-ethyl-2-methyl-propyl)-phenyl ester (5 g, 0.01 mol, having purity 96.2% by HPLC) in methanol (10 ml), methanolic solution of oxalic acid dihydrate (1.68 g in 10 ml methanol) was added at ambient temperature and stirred for 15 minutes. Solvents were distilled off from the reaction mixture. To the residue ethyl acetate was added and resulting solid was filtered to give 3.93 g of title compound having purity 98.3% by HPLC.

Step II: Preparation of [1R,2R]toluene-4-sulfonic Acid 3-(3-dimethylamino-1-ethyl-2-methyl-propyl)-phenyl Ester To a suspension of [1R,2R]toluene-4-sulfonic acid 3-(3-dimethylamino-1-ethyl-2-methyl-propyl)-phenyl ester oxalate salt (2 g) in dichloromethane (10 ml), 2N hydrochloric acid (2.7 ml) was added and stirred for 30 minutes. Layers were separated and organic layer was washed with water. Solvent was distilled off from the organic layer to give 1.29 g of the title compound having purity 98.2% by HPLC.

Example 17

Preparation of 3-(3-Dimethylamino-1-ethyl-2-methyl-propyl)-phenol

To a stirred solution of [1RS,2RS]-toluene-4-sulfonic acid 3-(3-dimethylamino-1-ethyl-2-methyl-propyl)-phenyl ester (9 g, 0.02 mol) and methanol (27 ml), a solution of sodium hydroxide (4 g, 0.10 mol) and water (18 ml) was added at 20-25° C. and mixture was stirred at 28-35° C. for 20 hours. Reaction mixture was further stirred at 45-50° C. for 6 hours and solvent was distilled off. Resulting residue was dissolved in demineralised water (30 ml) at ambient temperature and washed with isopropyl ether (2×10 ml). Aqueous layer was separated and aqueous hydrochloric acid (7.3 ml, 30%) was added at 20-25° C. reaction mixture was saturated with sodium chloride and extracted with ethyl acetate (2×50 ml). All ethyl acetate extracts were combined, washed with water, dried and solvent was distilled off to give 4.24 g of title compound.

Example 18

Preparation of Tapentadol

Method A:
A mixture of [1R,2R]toluene-4-sulfonic acid 3-(3-dimethylamino-1-ethyl-2-methyl-propyl)-phenyl ester (27 g, 0.07 mol), methanol (216 ml), demineralised water (54 ml) and potassium hydroxide (16.2 g, 0.29 mol) was refluxed for 30 minutes and solvent was distilled off at 50° C./150 mmHg. Isopropyl ether (50 ml) and demineralised water (25 ml) were added and stirred for 20 minutes. Aqueous layer was separated and aqueous hydrochloric acid (35 ml, 15%) was added to the reaction mixture till pH 9.5. Resulting aqueous layer was saturated with sodium chloride and extracted with ethyl acetate (200 ml). Aqueous layer was separated and 15% hydrochloric acid (20 ml) was added to the aqueous layer till pH 7. Resulting reaction mixture extracted with ethyl acetate (100 ml). All organic extracts were combined and washed with water. Combined organic layer was dried and solvent was distilled off to give 14 g (88%) of the title compound.

Method B:
A mixture of [1R,2R]toluene-4-sulfonic acid 3-(3-dimethylamino-1-ethyl-2-methyl-propyl)-phenyl ester (27 g, 0.07 mol), methanol (216 ml), demineralised water (54 ml) and sodium hydroxide (11.5 g, 0.29 mol) was stirred at 28-35° C. for 20 hours and solvent was distilled off at 50° C. 150 mmHg. Isopropyl ether (50 ml) and demineralised water (25 ml) were added to the reaction mixture at ambient temperature and stirred for 20 minutes. Aqueous layer was separated and aqueous hydrochloric acid (35 ml, 15%) was added to the reaction mixture till pH 10-11. Resulting aqueous layer was saturated with sodium chloride and extracted with ethyl acetate (200 ml). Aqueous layer was separated and 15% hydrochloric acid (20 ml) was added to the aqueous layer till pH 7. Resulting reaction mixture extracted with ethyl acetate (100 ml). All organic extracts were combined and washed with water. Combined organic layer was dried and solvent was distilled off to give 13 g (81.7%) of the title compound.

Method C:
A mixture of [1R,2R]toluene-4-sulfonic acid 3-(3-dimethylamino-1-ethyl-2-methyl-propyl)-phenyl ester (42 g, 0.11 mol), methanol (336 ml), demineralised water (84 ml) and sodium hydroxide (17.92 g, 0.45 mol) was stirred at 28-35° C. for 20 hours and solvents were distilled off at 50° C./150 mmHg. Isopropyl ether (105 ml) and demineralised water (84 ml) were added to the resulting residue and stirred for 20 minutes. Aqueous layer was separated and concentrated hydrochloric acid (20%) was added to the aqueous layer at 5-10° C. to attain pH 10-11. Thereafter aqueous layer was saturated with sodium chloride (30 g) and extracted with dichloromethane (3×200 ml). Organic extracts were combined, washed with water (2×50 ml), dried and solvent was distilled off to give 22.3 g (90%) of the title compound.

Method D:
To a stirred solution of [1R,2R]toluene-4-sulfonic acid 3-(3-dimethylamino-1-ethyl-2-methyl-propyl)-phenyl ester (3.01 kg, 8.02 mol) and methanol (24 L), a solution of sodium hydroxide (1.3 kg, 32.5 mol) and water (6 L) was added at 20-25° C. The reaction mixture was stirred at 28-35° C. for 20 hours and then at 45-50° C. for 6 hours. Solvent was distilled off from the reaction mixture. Resulting residue was dissolved in demineralised water (6 L) and washed with isopropyl ether (2×3 L). Aqueous layer was separated and aqueous hydrochloric acid (2.5 L, 30%) added at 20-25° C., saturated with sodium chloride and extracted with ethyl acetate (2×15 L). All ethyl acetate extracts were combined, washed with water, dried and solvents were distilled off to give 1.5 kg of the title compound as an oil.

$^1$H NMR δ (CDCl$_3$): 6.58-7.10 (4H, m, ArH), 2.83 (2H, m, NCH$_2$), 2.75 & 2.65 (3H, d each, NCH$_3$), 2.23 (1H, m, ArCH), 2.10 (1H, m, CH$_3$CH), 1.52 & 1.82 (1H, m each, CH$_2$CH$_3$ at 13), 1.26 (3H, d, CHCH$_3$), 0.70 (3H, t, CH$_2$CH$_3$)

Mass analysis (m/e) shows M$^{+1}$ peak at 222.16

Example 19

Preparation of 3-(3-dimethylamino-1-ethyl-2-methyl-propyl)-phenol Hydrochloride

To stirred solution of 3-(3-dimethylamino-1-ethyl-2-methyl-propyl)-phenol (4 g, 0.02 mol) in dichloromethane (20 ml), isopropyl ether hydrochloride (6 ml) was added at ambient temperature and stirred for 30 minutes. Solvents were distilled off from the reaction mixture. To the residue isopropyl ether (8 ml) was added and stirred for 15 minutes. Solvent was distilled off from the mixture to give 4.3 g of the title compound.

Example 20

Preparation of Tapentadol Hydrochloride

Method A:
To a solution of tapentadol (14 g, 0.06 mol) in dichloromethane (70 ml), isopropyl ether hydrochloride (21 ml) was added at ambient temperature and stirred for 30 minutes. Solvents were distilled off from the reaction mixture. Isopropyl ether (70 ml) was added to resulting residue and stirred for 15 minutes and solvent was distilled off. Isopropanol (70 ml) was added to the residue, heated to 60-70° C. till dissolution. Reaction mixture was cooled to −5° C. for 2 hours, filtered and dried to give 9.8 g of the title compound which was slurried in acetone (50 ml) at reflux. The reaction mixture was cooled and filtered to give 9 g of the title compound having purity 95.6% by HPLC.

Method B:
To stirred solution of tapentadol free base (1.5 kg, 6.77 mol) in dichloromethane (4.5 L), ethyl acetate hydrochloride (1.98 L) was added at 0-5° C. and stirred for 1 hour. Thereafter, solvent was distilled off from the reaction mixture. Isopropanol (1.5 L) was added to the residue and heated to 70-80° C. to dissolve. Mixture was cooled to −5° C. for 2 hours, filtered and dried. Resulting product was slurried in acetone (1 L), filtered and dried to give 1.08 kg of the title compound.

Method C:
To stirred solution of tapentadol free base (21 g, 0.09 mol) in dichloromethane (105 ml), isopropyl ether hydrochloride (32 ml) was added and stirred for 30 minutes. Solvents were distilled off from the reaction mixture and isopropyl ether (105 ml) was added to the residue. Mixture was stirred for 15 minutes and solvents were distilled off. Acetonitrile (100 ml) was added to the resulting residue, heated to 65-70° C. and stirred for 15 hours. Reaction mixture was cooled to −5° C., and filtered and dried to give 16.2 g of the title compound which was again purified with acetonitrile to give title compound having purity 99.8% by HPLC; and 100% by chiral HPLC.

$[\alpha]_D^{RT}=-27.5$ (c=0.97%; methanol)

Example 21

Purification of Tapentadol Hydrochloride

A slurry of tapentadol hydrochloride (1.08 kg) and acetonitrile (6.1 L) was stirred at 80° C. for 3 hours and cooled to ambient temperature. Resulting product was filtered and dried to give 0.7 kg of the title compound having purity 99.71% by HPLC; and 99.8% by chiral HPLC.

We claim:

1. A process for the preparation of a 1-phenyl-3-dimethylaminopropane derivative of formula I:

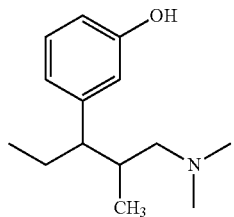

Formula I an isomer thereof, an enantiomer thereof, a diastereomer thereof, a racemate thereof, a solvate thereof, a hydrate thereof, or a pharmaceutically acceptable salt thereof; said method comprising:
a) converting 1-(3-hydroxy-phenyl)-propan-1-one of formula II,

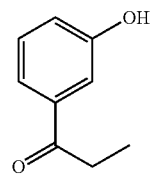

Formula II into a compound of general formula III,

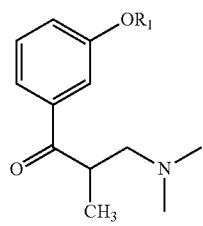

Formula III wherein $R_1$ is selected from —$SO_2R_2$; $R_2$ is selected from hydrogen, straight chain or branched alkyl, aryl, aralkyl, alkaryl, heteroalkyl, heteroaryl, wherein $R_2$ is is substituted or unsubstituted;
b) reacting the compound of formula III with a suitable organometallic reagent to give a hydroxyl compound of formula IV,

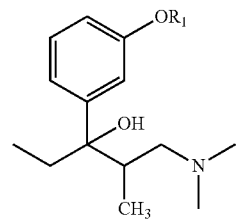

Formula IV wherein $R_1$ is as defined above;
c) optionally, reacting the hydroxyl compound of formula IV with a suitable acid to form a corresponding salt of the hydroxyl compound of formula IV;
d) dehydrating the hydroxyl compound of formula IV or the corresponding salt thereof using a suitable dehydrating agent to give an alkene compound of formula V,

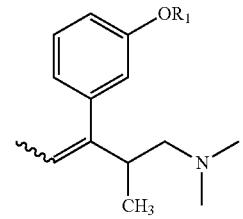

Formula V wherein $R_1$ is as defined above;
e) hydrogenating the alkene compound of formula V using a suitable reagent to give a compound of formula VI,

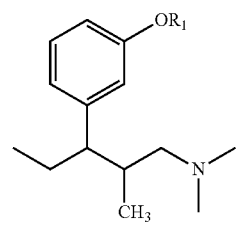

Formula VI wherein $R_1$ is as defined above; and
f) deprotecting the compound of formula VI with a suitable deprotecting reagent to give the compound of formula I or a pharmaceutically acceptable salt thereof.

2. The process according to claim 1, wherein in step b), the suitable organometallic reagent is ethyl lithium or an ethyl magnesium halide.

3. The process according to claim 1, wherein in step c), the suitable acid is selected from the group consisting of:
the inorganic acids hydrochloric acid, sulfuric acid, nitric acid, phosphoric acid, and perchloric acid;
the achiral organic acids formic acid and acetic acid and
the chiral organic acids camphor sulfonic acid, mandelic acid, and substituted or unsubstituted tartaric acid; and
mixtures thereof.

4. The process according to claim 1, wherein in step d), the suitable dehydrating agent is selected from the group consisting of oxalic acid, terphthalic acid, citric acid hydrochloric acid, sulfuric acid, hydroiodic acid, hydrobromic acid, phosphoric acid, polyphosphoric acid, boric acid; p-toluenesulfonic acid, benzenesulfonic acid, methanesulfonic acid;

alkali or alkaline metal sulfates thionyl chloride pyridine complex, phosphorus oxychloride pyridine complex, methanesulfonyl chloride pyridine complex, trifluoroacetic anhydride dimethyl amino pyridine complex, silica, alumina, titanium oxide, niobium pentoxide; nafion, amberlyst, zeolites, heteropolyacids, and mixed metal oxides.

5. The process according to claim 1, wherein in step e), the suitable reagent is a heterogeneous or homogeneous, chiral or achiral hydrogenation catalyst.

6. The process according to claim 1, wherein in step f), the deprotecting reagent is selected from the group consisting of:
   an organic base of general formula NR'R"R'";
      wherein R', R" and R'" can be the same or different and are independently selected from the group consisting of alkyl, aryl, aralkyl, alkaryl, heteroalkyl and heteroaryl; and
   an inorganic base selected from the group consisting of alkali or alkaline earth metal hydroxides, carbonates, bicarbonates, hydrides and alkoxides.

7. The process according to claim 1, wherein in step a), converting 1-(3-hydroxy-phenyl)-propan-1-one of formula II in to the compound of formula III comprises:
   i. protecting the hydroxyl group of 1-(3-hydroxy-phenyl)-propan-1-one of formula II with a suitable reagent; and
   ii. aminomethylating the propanoyl moiety of the compound of formula II using a suitable aminomethyling agent;
   wherein said protecting step and said aminomethylating step may be carried out in any order.

8. The process according to claim 7, wherein in step a), the suitable reagent is an optionally substituted sulfonyl halide or an optionally substituted sulfonyl anhydride;
   said sulfonyl halide being selected from the group consisting of a linear or branched alkylsulfonyl halide, an arylsulfonyl halide, an aralkylsulfonyl halide, an alkarylsulfonyl halide, a heteroalkylsulfonyl halide, a heteroarylsulfonyl halide, p-toluenesulfonyl halide, benzenesulfonyl halide, ortho-chlorobenzenesulfonyl halide, meta-chlorobenzenesulfonyl halide and para-chlorobenzenesulfonyl halide; and
   said sulfonyl anhydride being selected from the group consisting of a linear or branched alkylsulfonyl anhydride, an arylsulfonyl anhydride, an aralkylsulfonyl anhydride, an alkarylsulfonyl anhydride, a heteroalkylsulfonyl anhydride, or a heteroarylsulfonyl anhydride.

9. The process according to claim 7, wherein in step b), the suitable aminomethyling agent is formaldehyde and dimethyl amine; or N-methyl-N-methylenemethane ammonium halide and acetyl halide.

10. A process for the preparation of tapentadol of formula Ia,

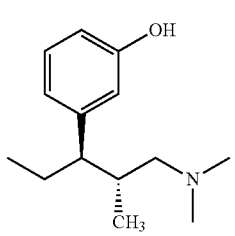

Formula Ia or a pharmaceutically acceptable salt thereof, comprising:
   a) resolving a compound of formula III using a suitable resolving agent to form a chiral compound of formula IIIa,

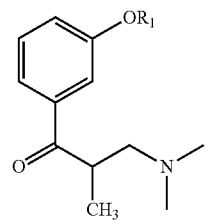

Formula III

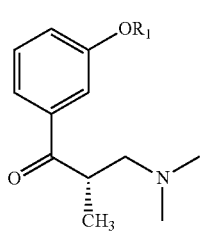

Formula IIIa wherein $R_1$ is $-SO_2R_2$;
wherein $R_2$ is selected from the group consisting of hydrogen, straight chain or branched alkyl, aryl, aralkyl, alkaryl, heteroalkyl, and heteroaryl; and
wherein $R_2$ is substituted or unsubstituted;

b) reacting the compound of formula IIIa with a suitable organometallic reagent to give a hydroxyl compound of formula IVa,

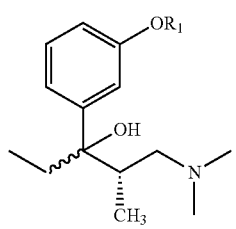

Formula IVa c) dehydrating the hydroxyl compound of formula IVa or a salt thereof, to give an alkene compound of formula Va;

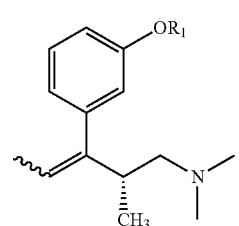

Formula Va d) hydrogenating the alkene compound of formula Va to give a compound of formula VIa, and

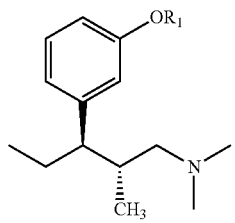

Formula VIa e) deprotecting the compound of formula VIa to give tapentadol of formula Ia or a pharmaceutically acceptable salt thereof.

11. The process according to claim 10, wherein the resolving agent is a chiral acid selected from the group consisting of dibenzoyl tartaric acid, camphor sulfonic acid, tartaric acid, di-tolyl tartaric acid, and mandelic acid.

12. The process according to claim 10, wherein, in step b), the suitable organometallic reagent is ethyl lithium or an ethyl magnesium halide.

13. The process according to claim 10, wherein, in step c), said dehydrating is carried out with a dehydrating agent selected from the group consisting of an achiral organic acid; an inorganic acid; a sulfonic acid; an alkali or alkaline earth metal sulfate; a pyridine complex; silica; alumina; titanium oxide; niobium pentoxide; nation; amberlyst; zeolites; heteropolyacids; and mixed metal oxides.

14. The process according to claim 10, wherein in step d), hydrogenating is carried out with a heterogeneous or homogeneous, chiral or achiral hydrogenation catalyst.

15. The process according to claim 1, wherein in step e), deprotecting is carried out with a reagent selected from the group consisting of:
an organic base of general formula NR'R''R''';
wherein R', R'' and R''' can be the same or different and are independently selected from the group consisting of alkyl, aryl, aralkyl, alkaryl, heteroalkyl and heteroaryl; and
an inorganic base selected from the group consisting of alkali or alkaline earth metal hydroxides, carbonates, bicarbonates, hydrides and alkoxides.

16. A compound selected from the group consisting of:
a) a compound of formula III:

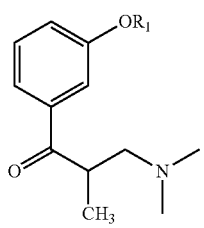

Formula III wherein $R_1$ is —$SO_2R_2$;
wherein $R_2$ is selected from the group consisting of hydrogen, straight chain or branched alkyl, aryl, aralkyl, alkaryl, heteroalkyl, and heteroaryl; and
wherein $R_2$ is substituted or unsubstituted;
isomers thereof, enantiomers thereof, diastereomers thereof, racemates thereof, salts thereof, solvates thereof, hydrates thereof; and mixtures thereof;

b) a compound of formula IV:

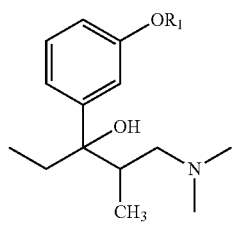

Formula IV wherein $R_1$ is —$SO_2R_2$;
wherein $R_2$ is selected from the group consisting of hydrogen, straight chain or branched alkyl, aryl, aralkyl, alkaryl, heteroalkyl, and heteroaryl; and
wherein $R_2$ is substituted or unsubstituted;
isomers thereof, enantiomers thereof, diastereomers thereof, racemates thereof, salts thereof, solvates thereof, hydrates thereof; and mixtures thereof; and c) a compound of formula V:

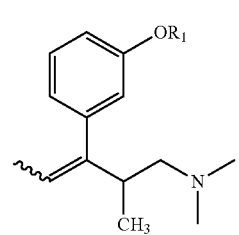

Formula V wherein $R_1$ is —$SO_2R_2$;
wherein $R_2$ is selected from the group consisting of hydrogen, straight chain or branched alkyl, aryl, aralkyl, alkaryl, heteroalkyl, and heteroaryl; and
wherein $R_2$ is substituted or unsubstituted;
isomers thereof, enantiomers thereof, diastereomers thereof, racemates thereof, salts thereof, solvates thereof, hydrates thereof; and mixtures thereof; and d) a compound of formula VI:

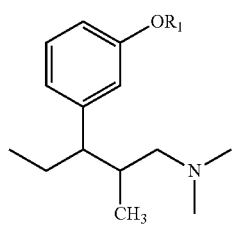

Formula VI wherein $R_1$ is —$SO_2R_2$;
wherein $R_2$ is selected from the group consisting of hydrogen, straight chain or branched alkyl, aryl, aralkyl, alkaryl, heteroalkyl, and heteroaryl; and
wherein $R_2$ is substituted or unsubstituted;
isomers thereof, enantiomers thereof, diastereomers thereof, racemates thereof, salts thereof, solvates thereof, hydrates thereof; and mixtures thereof.

17. The compound of claim 16, wherein said compound is a compound of formula IIIa:
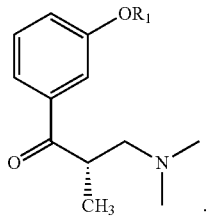
Formula IIIa
18. The compound of claim 16, wherein said compound is a compound of formula IVa:
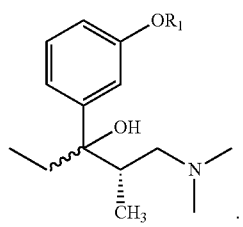
Formula IVa
19. The compound of claim 16, wherein said compound is a compound of formula Va:
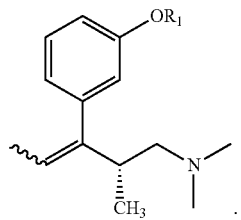
Formula Va
20. The compound of claim 16, wherein said compound is a compound of formula VIa:
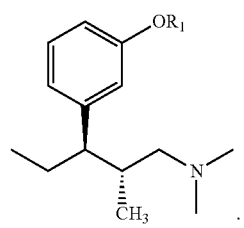
Formula VIa
* * * * *